(12) United States Patent
van der Burg et al.

(10) Patent No.: US 7,128,073 B1
(45) Date of Patent: Oct. 31, 2006

(54) METHOD AND DEVICE FOR LEFT ATRIAL APPENDAGE OCCLUSION

(75) Inventors: Erik J. van der Burg, Sunnyvale, CA (US); Dino De Cicco, Sunnyvale, CA (US); Andrew G. C. Frazier, Sunnyvale, CA (US); Alex K. Khairkahan, Palo Alto, CA (US); Marc S. Kriedler, Sunnyvale, CA (US); Michael D. Lesh, Mill Valley, CA (US); Chad C. Roue, Fremont, CA (US)

(73) Assignee: ev3 Endovascular, Inc., Plymouth, MN (US)

( * ) Notice: Subject to any disclaimer, the term of this patent is extended or adjusted under 35 U.S.C. 154(b) by 0 days.

(21) Appl. No.: 09/435,562

(22) Filed: Nov. 8, 1999

Related U.S. Application Data

(63) Continuation-in-part of application No. 09/187,200, filed on Nov. 6, 1998, now Pat. No. 6,152,144.

(51) Int. Cl.
*A61B 17/00* (2006.01)
*A61B 29/00* (2006.01)

(52) U.S. Cl. ..................... 128/887; 606/200

(58) Field of Classification Search .............. 606/1, 606/151, 190–200, 213, 110, 113, 114, 127, 606/128, 159, 167, 170, 171, 108, 157; 627/1.1–1.54, 627/11.11, 901, 921; 128/887
See application file for complete search history.

(56) References Cited

U.S. PATENT DOCUMENTS

| | | | |
|---|---|---|---|
| 3,402,710 A | 9/1968 | Paleschuck | |
| 3,540,431 A * | 11/1970 | Uddin | 606/200 |
| 3,557,794 A | 1/1971 | Van Patten | |
| 3,638,652 A | 2/1972 | Kelly | |
| 3,844,302 A | 10/1974 | Klein | |
| 3,874,388 A | 4/1975 | King et al. | |
| 4,007,743 A | 2/1977 | Blake | |
| 4,309,776 A | 1/1982 | Berguer | |
| 4,341,218 A | 7/1982 | Ü | |
| 4,603,693 A | 8/1986 | Contra et al. | |
| 4,611,594 A | 9/1986 | Grayhack et al. | |
| 4,665,906 A | 5/1987 | Jervis | |
| 4,681,588 A | 7/1987 | Ketharanathan | |
| 4,710,192 A | 12/1987 | Liotta et al. | |
| 4,832,055 A | 5/1989 | Palestrant | |
| 4,917,089 A | 4/1990 | Sideris | |
| 4,921,484 A | 5/1990 | Hillstead | |
| 5,041,090 A | 8/1991 | Scheglov et al. | |

(Continued)

FOREIGN PATENT DOCUMENTS

WO    WO 95/22359    8/1995

(Continued)

OTHER PUBLICATIONS

PCT Search Report from co-pending Application PCT/US02/33808 dated May 20, 2003.

(Continued)

*Primary Examiner*—Glenn K. Dawson
(74) *Attorney, Agent, or Firm*—Knobbe, Martens, Olson & Bear, LLP

(57) ABSTRACT

Disclosed is an occlusion device for use in a body lumen such as the left atrial appendage. The occlusion device includes an occlusion member and may also include a stabilizing member. The stabilizing member inhibits compression of the left atrial appendage, facilitating tissue in-growth onto the occlusion member. Methods are also disclosed.

62 Claims, 20 Drawing Sheets

U.S. PATENT DOCUMENTS

| | | | |
|---|---|---|---|
| 5,042,707 A | 8/1991 | Taheri | |
| 5,064,435 A | 11/1991 | Porter | |
| 5,071,407 A | 12/1991 | Termin et al. | |
| 5,078,736 A | 1/1992 | Behl | |
| 5,098,440 A | 3/1992 | Hillstead | |
| 5,108,420 A | 4/1992 | Marks | |
| 5,108,474 A * | 4/1992 | Riedy et al. | 55/485 |
| 5,116,360 A | 5/1992 | Pinchuk et al. | |
| 5,122,136 A | 6/1992 | Guglielmi et al. | |
| 5,171,259 A | 12/1992 | Inoue | |
| 5,176,692 A | 1/1993 | Wilk et al. | |
| 5,192,301 A | 3/1993 | Kamiya et al. | |
| 5,234,458 A * | 8/1993 | Metais | 606/200 |
| 5,258,042 A | 11/1993 | Mehta | |
| 5,284,488 A | 2/1994 | Sideris | |
| 5,304,184 A | 4/1994 | Hathaway et al. | |
| 5,306,234 A | 4/1994 | Johnson | |
| 5,334,217 A | 8/1994 | Das | |
| 5,350,398 A | 9/1994 | Pavcnik et al. | |
| 5,350,399 A | 9/1994 | Erlebacher et al. | |
| 5,375,612 A * | 12/1994 | Cottenceau et al. | 128/899 |
| 5,417,699 A | 5/1995 | Klein et al. | |
| 5,425,744 A | 6/1995 | Fagan et al. | |
| 5,433,727 A | 7/1995 | Sideris | |
| 5,443,454 A | 8/1995 | Tanabe et al. | |
| 5,443,478 A | 8/1995 | Purdy | |
| 5,451,235 A | 9/1995 | Lock et al. | |
| 5,464,408 A | 11/1995 | Duc | |
| 5,490,856 A | 2/1996 | Person et al. | |
| 5,522,790 A * | 6/1996 | Moll et al. | 606/204 |
| 5,522,836 A | 6/1996 | Palermo | |
| 5,527,322 A | 6/1996 | Klein et al. | |
| 5,527,338 A | 6/1996 | Purdy | |
| 5,569,204 A | 10/1996 | Cramer | |
| 5,614,204 A | 3/1997 | Cochrum | |
| 5,634,936 A | 6/1997 | Linden et al. | |
| 5,634,942 A | 6/1997 | Chevillon et al. | |
| 5,643,282 A | 7/1997 | Kieturakis | |
| 5,643,292 A | 7/1997 | Hart | |
| 5,669,933 A | 9/1997 | Simon et al. | |
| 5,693,067 A | 12/1997 | Purdy | |
| 5,700,285 A | 12/1997 | Myers et al. | |
| 5,702,421 A | 12/1997 | Schneidt | |
| 5,709,224 A | 1/1998 | Behl et al. | |
| 5,709,707 A | 1/1998 | Lock et al. | |
| 5,725,552 A | 3/1998 | Kotula et al. | |
| 5,725,568 A | 3/1998 | Hastings | |
| 5,733,294 A | 3/1998 | Forber et al. | |
| 5,735,290 A | 4/1998 | Sterman et al. | |
| 5,749,880 A | 5/1998 | Banas et al. | |
| 5,749,894 A | 5/1998 | Engelson | |
| 5,766,219 A | 6/1998 | Horton | |
| 5,776,097 A | 7/1998 | Massoud | |
| 5,782,860 A | 7/1998 | Epstein et al. | |
| 5,800,457 A | 9/1998 | Gelbfish | |
| 5,800,512 A | 9/1998 | Lentz et al. | |
| 5,830,228 A | 11/1998 | Knapp et al. | |
| 5,836,968 A | 11/1998 | Simon et al. | |
| 5,843,118 A | 12/1998 | Sepetka et al. | |
| 5,849,005 A | 12/1998 | Garrison et al. | |
| 5,853,422 A * | 12/1998 | Huebsch et al. | 606/213 |
| 5,865,791 A | 2/1999 | Whayne et al. | |
| 5,879,366 A | 3/1999 | Shaw et al. | |
| 5,891,558 A | 4/1999 | Bell et al. | |
| 5,904,680 A | 5/1999 | Kordis et al. | |
| 5,906,207 A | 5/1999 | Shen | |
| 5,911,734 A | 6/1999 | Tsugita et al. | |
| 5,928,260 A * | 7/1999 | Chin et al. | 606/200 |
| 5,935,148 A | 8/1999 | Villar et al. | |
| 5,961,545 A * | 10/1999 | Lentz et al. | 623/1 |
| 5,993,483 A | 11/1999 | Gianotti | |
| 6,004,348 A | 12/1999 | Banas et al. | |
| 6,007,557 A | 12/1999 | Ambrisco et al. | |
| 6,013,093 A | 1/2000 | Nott et al. | |
| 6,063,070 A | 5/2000 | Eder | |
| 6,076,012 A | 6/2000 | Swanson et al. | |
| 6,079,414 A | 6/2000 | Roth | |
| 6,080,182 A | 6/2000 | Shaw et al. | |
| 6,096,053 A | 8/2000 | Bates | |
| 6,110,243 A * | 8/2000 | Wnenchak et al. | 55/379 |
| 6,123,715 A | 9/2000 | Amplatz | |
| 6,124,523 A * | 9/2000 | Banas et al. | 623/1.15 |
| 6,132,438 A | 10/2000 | Fleischman et al. | |
| 6,139,573 A | 10/2000 | Sogard et al. | |
| 6,152,144 A | 11/2000 | Lesh et al. | |
| 6,156,055 A | 12/2000 | Ravenscroft | |
| 6,171,329 B1 | 1/2001 | Shaw et al. | |
| 6,179,859 B1 | 1/2001 | Bates et al. | |
| 6,231,561 B1 | 5/2001 | Frazier et al. | |
| 6,258,115 B1 * | 7/2001 | Dubrul | 606/200 |
| 6,277,138 B1 | 8/2001 | Levinson et al. | |
| 6,290,674 B1 | 9/2001 | Roue et al. | |
| 6,312,407 B1 | 11/2001 | Zadno-Azizi et al. | |
| 6,328,727 B1 | 12/2001 | Frazier et al. | |
| 6,346,116 B1 | 2/2002 | Brooks et al. | |
| 6,368,338 B1 | 4/2002 | Kónya et al. | |
| 6,371,971 B1 | 4/2002 | Tsugita et al. | |
| 6,391,044 B1 | 5/2002 | Yadav et al. | |
| 6,402,746 B1 | 6/2002 | Whayne et al. | |
| 6,419,669 B1 | 7/2002 | Frazier et al. | |
| 6,447,530 B1 | 9/2002 | Ostrovsky et al. | |
| 6,468,291 B1 | 10/2002 | Bates et al. | |
| 6,551,303 B1 * | 4/2003 | Van Tassel et al. | 604/508 |
| 6,837,901 B1 | 1/2005 | Rabkin et al. | |
| 2001/0034537 A1 | 10/2001 | Shaw et al. | |
| 2002/0062133 A1 | 5/2002 | Gilson et al. | |
| 2002/0111647 A1 | 8/2002 | Khairkhahan et al. | |
| 2002/0138094 A1 | 9/2002 | Borillo et al. | |
| 2002/0138097 A1 | 9/2002 | Ostrovsky et al. | |
| 2003/0204203 A1 | 10/2003 | Khairkhahan et al. | |
| 2004/0034366 A1 | 2/2004 | Van der Burg et al. | |

FOREIGN PATENT DOCUMENTS

| | | |
|---|---|---|
| WO | WO 96/40356 | 12/1996 |
| WO | WO 98/27868 | 7/1998 |
| WO | WO 99/23976 | 5/1999 |
| WO | WO 99/44510 | 9/1999 |
| WO | WO 99/44510 | 10/1999 |
| WO | WO 00/16705 | 3/2000 |
| WO | WO 00/67669 | 11/2000 |
| WO | WO 01/15629 A1 | 3/2001 |
| WO | WO 01/30266 A1 | 5/2001 |
| WO | WO 01/30267 A1 | 5/2001 |
| WO | WO 01/30268 A1 | 5/2001 |

OTHER PUBLICATIONS

Written Opinion for co-pending PCT/US02/33808 dated Nov. 17, 2003.

International Search Report and Written Opinion from PCT/US2004/008109 with a mailing date of Aug. 3, 2004.

Specifications, Claims, and Figures from U.S. Appl. No. 10/802,395, filed Mar. 17, 2004, examiner presently unknown.

PCT Search Report for co-pending Application PCT/US99/26325 dated Feb. 15, 2000.

* cited by examiner

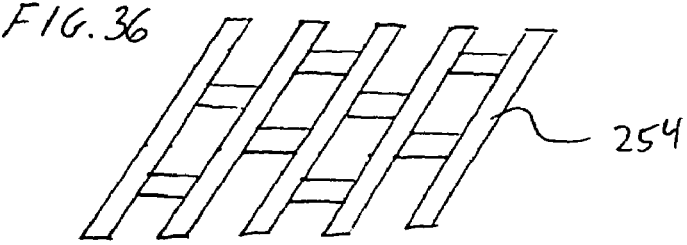
FIG. 36
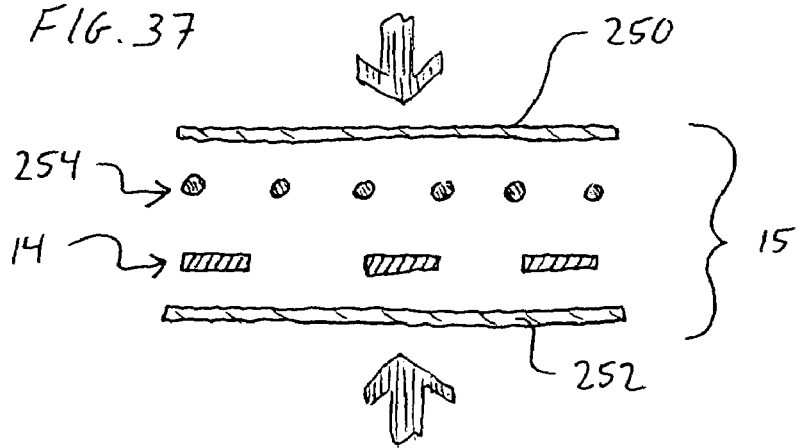
FIG. 37
FIG. 38
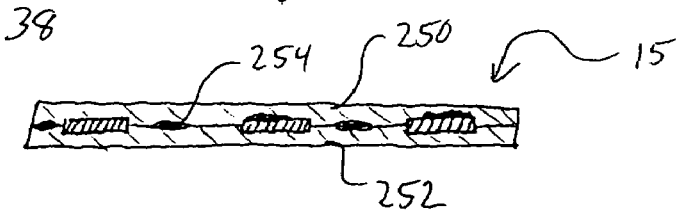
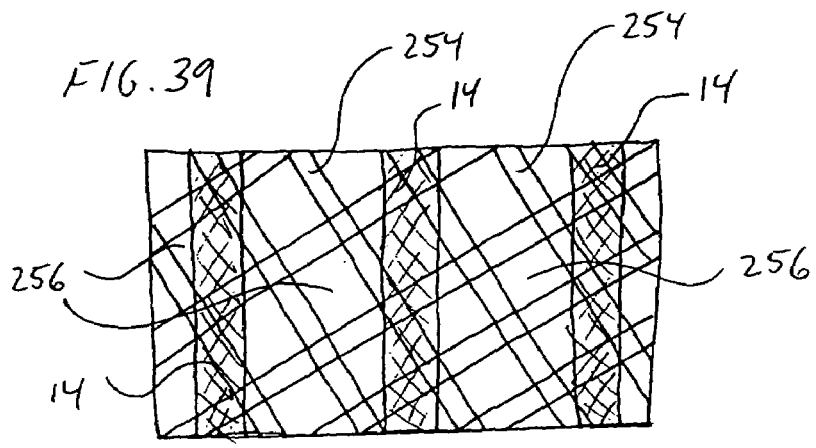
FIG. 39

METHOD AND DEVICE FOR LEFT ATRIAL APPENDAGE OCCLUSION

This is a continuation-in-part of U.S. patent application Ser. No. 09/187,200, filed Nov. 6, 1998, now U.S. Pat. No. 6,152,144, the disclosure of which is incorporated in its entirety herein by reference.

BACKGROUND OF THE INVENTION

Embolic stroke is the nation's third leading killer for adults, and is a major cause of disability. There are over 700,000 strokes per year in the United States alone. Of these, roughly 100,000 are hemoragic, and 600,000 are ischemic (either due to vessel narrowing or to embolism). The most common cause of embolic stroke emanating from the heart is thrombus formation due to atrial fibrillation. Approximately 80,000 strokes per year are attributable to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. Atrial fibrillation is associated with a 500 percent greater risk of stroke due to the condition. A patient with atrial fibrillation typically has a significantly decreased quality of life due, in part, to the fear of a stroke, and the pharmaceutical regimen necessary to reduce that risk.

For patients who develop atrial thrombus from atrial fibrillation, the clot normally occurs in the left atrial appendage (LAA) of the heart. The LAA is a cavity which looks like a small finger or windsock and which is connected to the lateral wall of the left atrium between the mitral valve and the root of the left pulmonary vein. The LAA normally contracts with the rest of the left atrium during a normal heart cycle, thus keeping blood from becoming stagnant therein, but often fails to contract with any vigor in patients experiencing atrial fibrillation due to the discoordinate electrical signals associated with AF. As a result, thrombus formation is predisposed to form in the stagnant blood within the LAA.

Blackshear and Odell have reported that of the 1288 patients with non-rheumatic atrial fibrillation involved in their study, 221 (17%) had thrombus detected in the left atrium of the heart. Blackshear J L, Odell J A., Appendage Obliteration to Reduce Stroke in Cardiac Surgical Patients With Atrial Fibrillation. Ann Thorac. Surg., 1996.61(2): 755–9. Of the patients with atrial thrombus, 201 (91%) had the atrial thrombus located within the left atrial appendage. The foregoing suggests that the elimination or containment of thrombus formed within the LAA of patients with atrial fibrillation would significantly reduce the incidence of stroke in those patients.

Pharmacological therapies for stroke prevention such as oral or systemic administration of warfarin or the like have been inadequate due to serious side effects of the medications and lack of patient compliance in taking the medication. Invasive surgical or thorascopic techniques have been used to obliterate the LAA, however, many patients are not suitable candidates for such surgical procedures due to a compromised condition or having previously undergone cardiac surgery. In addition, the perceived risks of even a thorascopic surgical procedure often outweigh the potential benefits. See Blackshear and Odell, above. See also Lindsay B D., Obliteration of the Left Atrial Appendage: A Concept Worth Testing, Ann Thorac. Surg., 1996.61(2):515.

Despite the various efforts in the prior art, there remains a need for a minimally invasive method and associated devices for reducing the risk of thrombus formation in the left atrial appendage.

SUMMARY OF THE INVENTION

There is provided in accordance with one aspect of the present invention, a method of occluding an atrial appendage. The method comprises the steps of inhibiting changes in the volume of the appendage, and occluding the opening to the appendage. The inhibiting changes in the volume step preferably comprises introducing a bulking element into the appendage to resist compression of the appendage wall. Preferably, the bulking element is an expandable element. In one embodiment, the introducing an expandable bulking element step comprises deploying a self-expandable bulking element from a deployment catheter. The occluding step comprises positioning an occlusion element to enclose the bulking element within the appendage.

In accordance with another aspect of the present invention, there is provided a method of facilitating cell growth onto an atrial appendage occlusion device. The method comprises the steps of positioning an occlusion device across the opening of the appendage, the occlusion device having a tissue attachment surface thereon. The method additionally comprises the step of resisting compression of the appendage at least during a tissue attachment period of time. The resisting step preferably comprises positioning a bulking structure within the appendage.

In accordance with a further aspect of the present invention, there is provided an occlusion device for implantation within the left atrial appendage. The occlusion device comprises an occluding member, enlargeable from a reduced cross section to an enlarged cross section. The occlusion device may further comprise a stabilizing member, enlargeable from a reduced cross section to an enlarged cross section. The enlarged cross section of the stabilizing member may be less than the enlarged cross section of the occlusion member. Any of the occluding member and stabilizing member structures disclosed herein can be provided as an occluding member alone, without the corresponding stabilizing member.

The occlusion device preferably further comprises a hub between the occlusion member and the stabilizing member. The occlusion member comprises an expandable frame, which may be made from at least two spokes. Each spoke has a first end and a second end, and the first end is attached to the hub. The spokes are movable between an axial orientation to provide a low profile such as for transluminal implantation, and a radially enlarged orientation such as during implantation within the appendage to occlude the appendage.

The stabilizing member comprises at least two elements which are movable from an axial orientation when the stabilizing member is in the reduced cross section to an inclined orientation when the stabilizing member is in the enlarged cross section. In one embodiment, each element comprises a proximal section, a distal section, and a bend in-between the proximal and distal sections when the stabilizing member is in the enlarged cross section. Preferably, the occlusion device further comprises at least one tissue attachment element such as a hook, spike or barb.

In accordance with a further aspect of the present invention, there is provided an occlusion device for occluding a tubular body structure. The occlusion device comprises a body, having a longitudinal axis. An expandable occlusion member is provided at a first position on the axis, and a stabilizing member is provided at a second position on the axis. The occlusion member comprises a plurality of spokes which are hingeably attached to the body and movable between an axial orientation and an inclined orientation.

Preferably, the occlusion member further comprises a polymeric membrane carried by the spokes. The stabilizing member comprises at least three radially outwardly movable elements. In one embodiment, a hinge is provided on the body between the occlusion member and the stabilizing member. One hinge construction comprises a helical coil.

In accordance with a further aspect of the present invention, there is provided a method of making an occlusion device. The method comprises the steps of providing a tube, having a first end, a second end, and a longitudinal axis. A plurality of axially extending slots are cut at a first position on the tube, to create a first plurality of longitudinal elements. A second plurality of axially extending slots are cut at a second position on the tube, to create a second plurality of longitudinal elements.

The method further comprises the steps of providing a radially outwardly directed bias on at least one of the first and second plurality of elements. A polymeric membrane may be attached to at least one of the first and second plurality of elements. In one embodiment, a hinge is provided on the tube in-between the first and second plurality of elements.

In accordance with a further aspect of the present invention, there is provided a method of occluding an atrial appendage. The method comprises the steps of introducing a stabilizing member into the appendage, for resisting compression of the appendage wall, and preventing rotation and axial migration of the implant, and positioning an occlusion member across the appendage. The introducing step preferably comprises introducing a radially expandable stabilizing member, and radially expanding the member within the appendage. The positioning step may comprise either positioning the occlusion member within the appendage, or positioning the occlusion member across an opening of the appendage. In one embodiment, the introducing and positioning steps are accomplished by introducing a deployment catheter within the appendage and deploying the stabilizing member and occluding member from the catheter. Preferably, the method further comprises the step of facilitating cell growth onto the occlusion member.

Further features and advantages of the present invention will become apparent to those of ordinary skill in the art in view of the detailed description of preferred embodiments which follows, when considered together with the attached drawings and claims.

BRIEF DESCRIPTION OF THE DRAWINGS

FIG. 36 is a schematic view of a bonding layer mesh for use in forming a composite barrier membrane in accordance with the present invention.

FIG. 37 is an exploded cross sectional view of the components of a composite barrier member in accordance with the present invention.

FIG. 38 is a cross sectional view through a composite barrier formed from the components illustrated in FIG. 37.

FIG. 39 is a top plan view of the composite barrier illustrated in FIG. 38.

DETAILED DESCRIPTION OF THE PREFERRED EMBODIMENT

Figure 1:
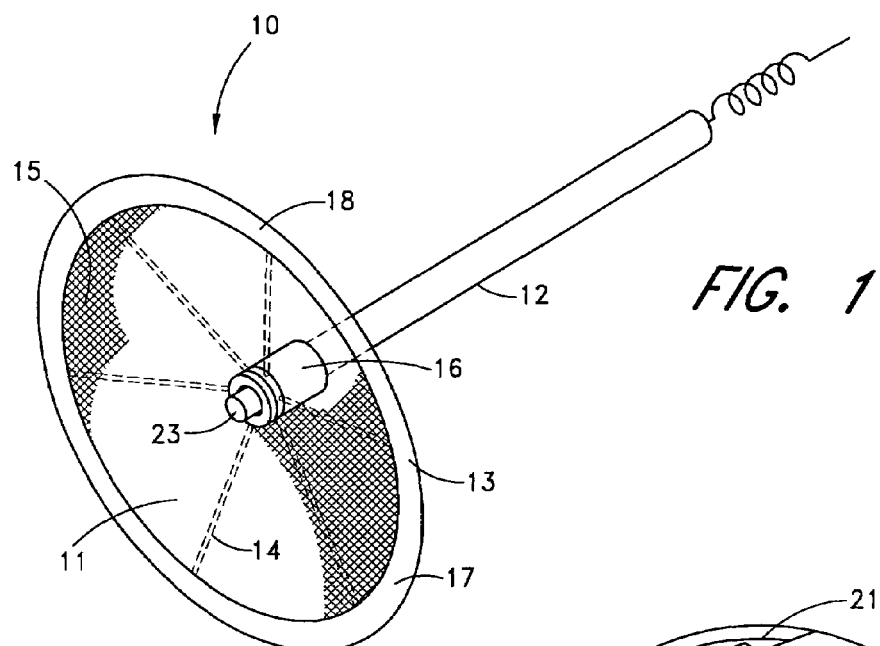
FIG. 1 shows a perspective view of an embodiment having features of the invention with an occluding member and a retention member.
Figure 2:
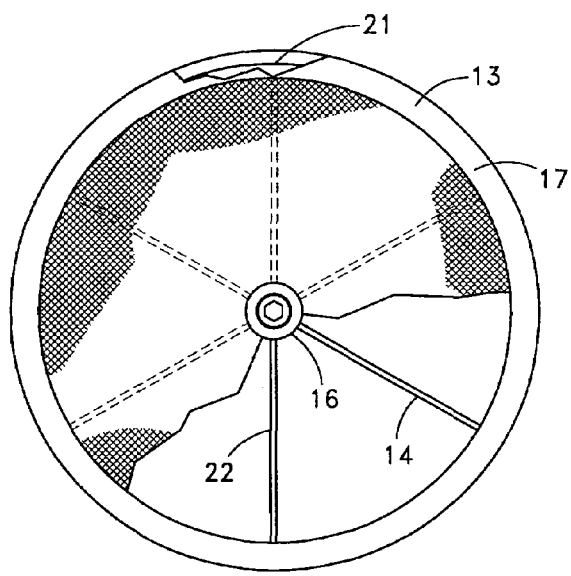
FIG. 2 shows an end view of the apparatus of FIG. 1 in partial section.
Figure 3:
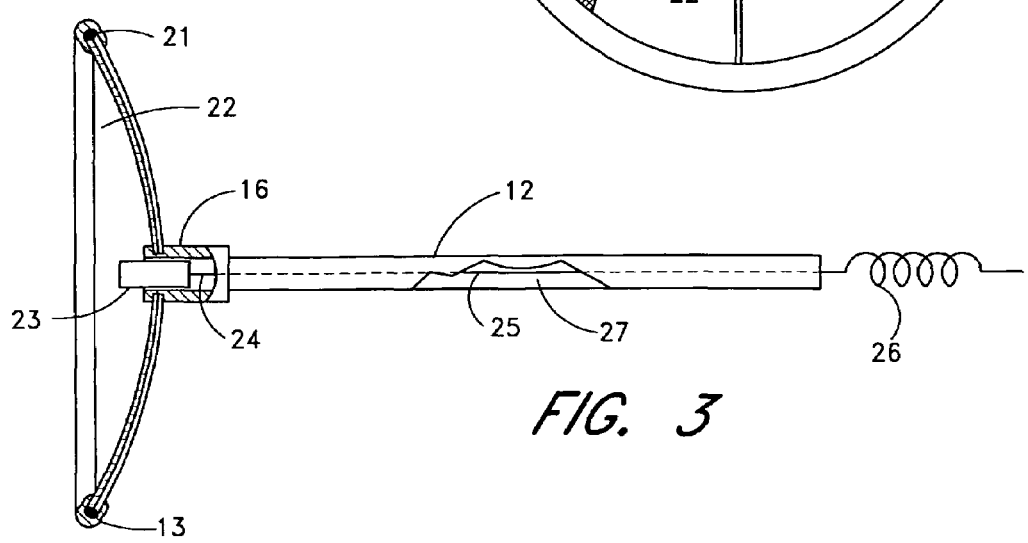
FIG. 3 shows a longitudinal cross-sectional view of the apparatus of FIGS. 1 and 2.

FIGS. 1–3 show an embodiment of an occluding device 10 having features of the invention where an occluding member 11 is secured to a retention member 12 that is arranged to fix the occluding member in a desired position within a body passageway or cavity. The occluding member 11 generally has disc shape with an outer rim 13 around the perimeter of a frame structure 14 which supports a barrier 15. The outer rim 13 can be circular or polygonal, or any other shape that is suitable for conforming to the inside surface of a body cavity. A hub 16 can be located near the center of the occluding member 11 which serves to connect the retention member 12 to the occluding member, in addition to other functions. The outer rim 13 is typically made from a soft polymer material 17 which permits flexibility of the outer rim and facilitates sealing of the outer rim against the inside surface of a body cavity or passageway. The barrier 15 can be a thin mesh or film of material which serves to block the passage of material within an area surrounded by the outer rim 13. The barrier 15 can be secured to the outer rim 13 along its entire perimeter 18 in order to achieve a complete seal therebetween and can be molded into the outer rim 13 or bonded thereto by a suitable method such as gluing, welding, sewing or other suitable method.

The outer rim 13 is at least partially supported by the frame structure 14 which connects the outer rim and the hub. The frame structure 14 can be made from one or more elements of high strength material such as stainless steel or MP35N, or may preferably be made from shape memory or pseudoelastic alloys such as NiTi, or any of a variety of known structural biodegradable materials (e.g. polyglycolic acid, poly lactic acid, poly-L-lactic acid and derivatives or copolymers such as PLGA). Preferably, the frame structure 14 is made from a material which can be self-expanding from a constrained configuration so that the occluding device 10 can be delivered to the deployment site in a low profile an flexible configuration which facilitates percutaneous delivery.

Preferably a radial hoop 21 is contained within the soft polymer material 17 of the outer rim 13 and serves to maintain the annular shape of the outer rim and facilitate radial expansion of the outer rim from a constrained position or configuration. The radial hoop 21 may be isolated within the soft polymer material 17 of the outer rim 13, or may be connected to at least some of the elements 22 of the frame structure 14, in order to have stronger mechanical joint between the outer rim and the frame structure. The radial hoop 21 is shown in a substantially circular configuration, but may also be polygonal or otherwise suitably shared, and may have connections or joints spaced thereon to facilitate contraction or folding of the device for non-invasive delivery.

In addition to connecting the retention member 12 and the occluding member 11, the hub 16 may serve to house a rotational coupling 23 which is connected to the proximal end 24 of a tissue penetrating shaft 25 within the retention member. The rotational coupling 23 allows the transfer of torque to the tissue penetrating shaft 25 which preferably has a helically shaped extension or distal extremity 26 which is configured to screw into tissue and be mechanically fixed thereto. Longitudinal movement of the tissue penetrating shaft 25 relative to the retention member 12 and hub 16 may be prevented by sizing a lumen 27 of the retention member which contains the tissue penetrating shaft such that the helically shaped extension 26 at the distal end is too large to pass through the lumen and the proximal end 24 of the tissue penetrating shaft is prevented from passing through the lumen by the rotational coupling attached thereto. The rotational coupling 23 may also be configured to be longitudinally captured by the hub 16 but still be rotatably disposed therein.

Figure 3A:
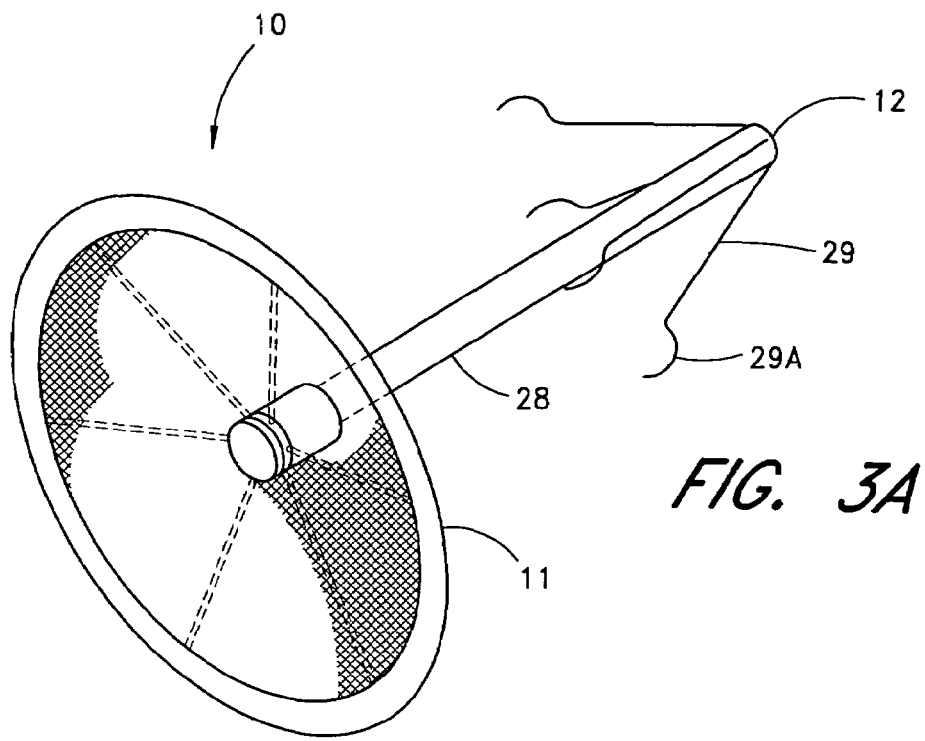
FIG. 3A shows a perspective view of an apparatus having features of the invention.
Figure 3B:
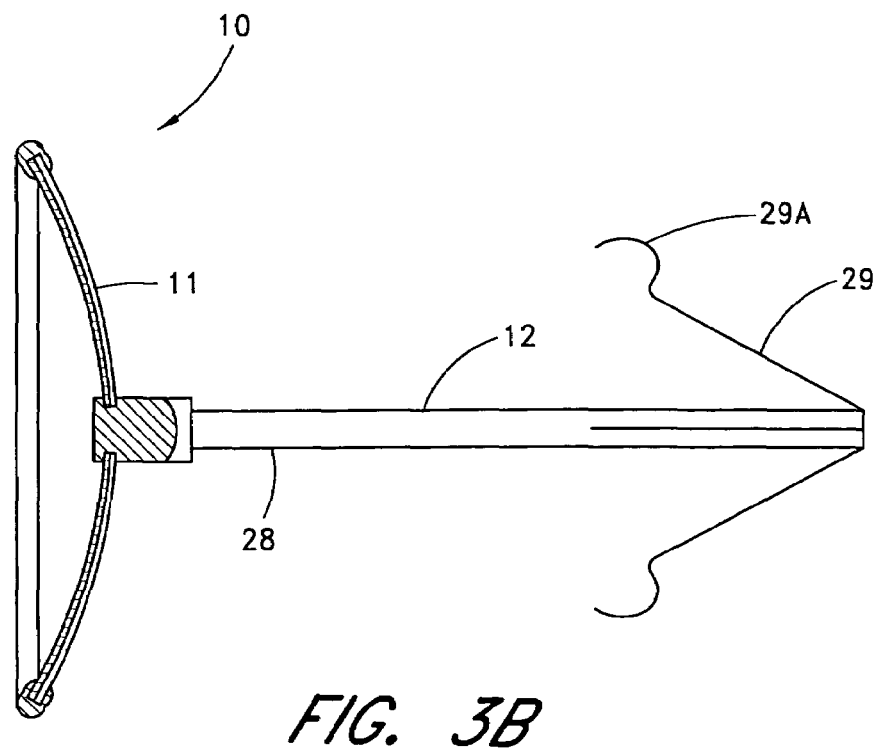
FIG. 3B shows an elevational view in partial section of the apparatus of FIG. 3A.

FIGS. 3A and 3B depict an alternative embodiment of an occluding device 10 having an occluding member 11 and a retention member 12. The retention member 12 has a shaft 28 and radially extending members 29 extending radially from a proximal end of the shaft. The radially extending members 29 serve to anchor the shaft 28 and the occluding member 11 by engaging the tissue surrounding the occluding device. Preferably, the radially extending members are self-expanding from a constricted state and are made of a pseudo elastic alloy such as NiTi, or a high strength material such as stainless steel. Although it is preferable for the radially extending members 29 to be self-expanding from a constricted state, they may also be expanded by use of shape memory properties or a radial outward force as would be provided by an inflatable balloon or the like. The shaft 28 can be a single element or made of multiple elements, and can be made from the same materials as the radially extending members or different materials such as polymers or polymer composites. The radially extending members 29 have a proximally directed bias at their radial extremities 29A so that the members readily fold down and move easily in a distal direction during insertion of the occluding device 10, but spring outward and aggressively engage surrounding tissue upon movement in a proximal direction. This configuration of the radially extending members 29 allows easy insertion into a body cavity, but prevents egress of the device 10 in and outward or proximal direction.

Figure 4:
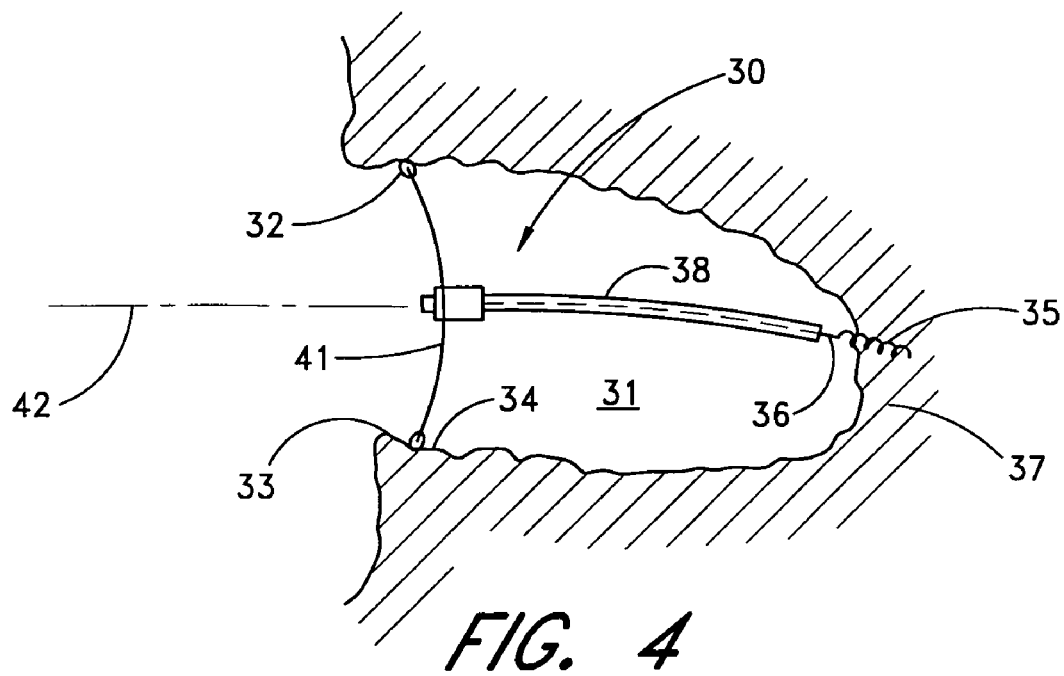
FIG. 4 shows an elevational view of an apparatus having features of the invention in a deployed state within a body cavity.

FIG. 4. depicts an occluding device 30 similar to that depicted in FIGS. 1–3 deployed within the left atrial appendage 31 of a patient. An outer rim or periphery 32 of the occluding device 30 is disposed adjacent the opening 33 of the left atrial appendage 31 in a position which allows for a substantial seal of the outer rim against the inside surface 34 of the LAA. A helically shaped distal extremity 35 of a tissue penetrating shaft 36 has been screwed into the wall tissue of the LAA and is mechanically secured thereto. A retention member 38 maintains the position of an occluding member 41 in a substantially perpendicular orientation with respect to a longitudinal axis of the LAA 42.

Figure 5:
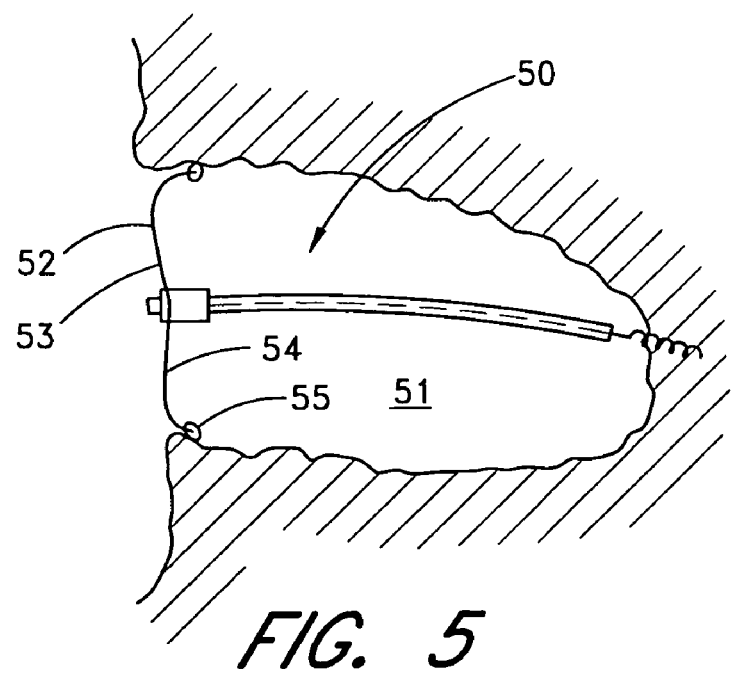
FIG. 5 shows an elevational view of an apparatus having features of the invention in a deployed state within a body cavity.

FIG. 5 depicts an occluding device similar to that depicted in FIGS. 1–4 deployed within a LAA 51 of a patient similar to what is shown in FIG. 4. The structure of an occluding member 52 of the embodiment as shown in FIG. 5 differs from that shown in FIG. 4 in that a barrier 53 and frame structure 54 of the embodiment of FIG. 5 protrudes proximally from a plane defined by an outer rim 55. This configuration may be useful for certain morphologies of patient's LAAs. One object of the invention is to create a smooth surface outside the body passageway or cavity in order to prevent turbulent flow or eddies of blood or other bodily fluid within the cavity or passageway. The alternative configuration of the occluding device 50 shown in FIG. 5 may be useful in this regard.

Figure 6:
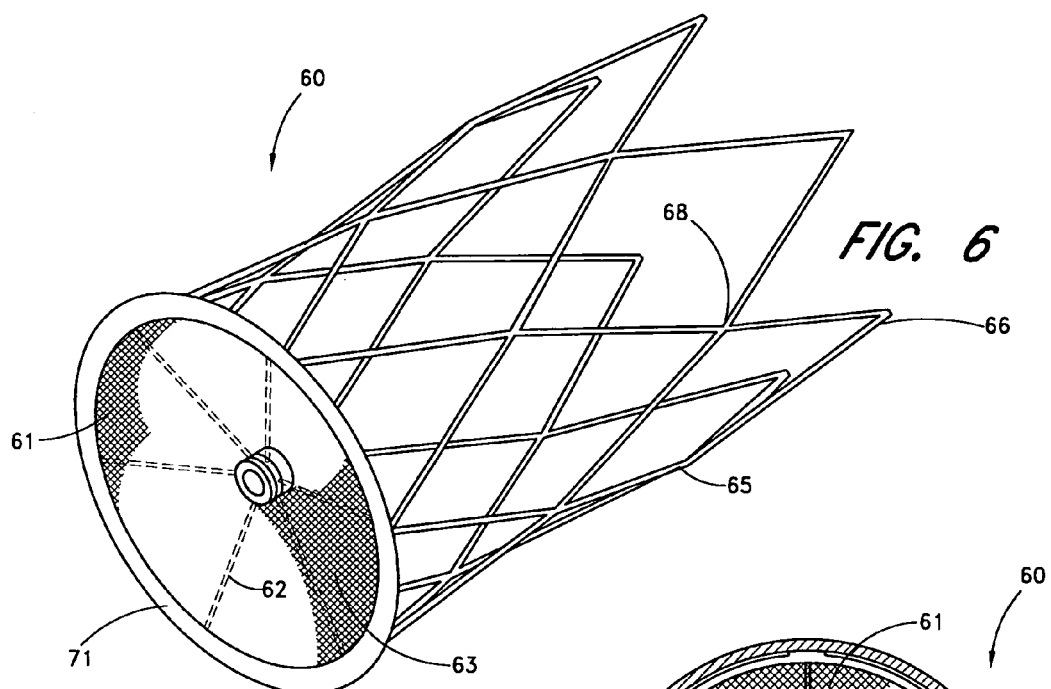
FIG. 6 shows a perspective view of an apparatus for sealing off a body cavity having features of the invention.

FIG. 6 shows an alternative embodiment of an occluding device 60 which has an occluding member 61, a frame structure 62, a barrier 63 and a retention member in the form of an expandable member 65 which has linked elements 66 that are preferably expandable from a constrained configuration. The expandable member 65 is generally cylindrical in shape and can have a series of circumferential linked elements 66 connected by links 68. Although FIG. 6 depicts the expandable member 65 as a series of linked elements 66, those skilled in the art will realize that a similar effect can be achieved with a single wire in a helical configuration or a plurality of wires in a mesh or braided configuration, or any other suitable configuration that can be self-expanding from a constrained configuration or expanding with the application of heat or other form of energy or force. For example, the expandable member 65 may be configured to be deployed by an outward radial force delivered from within the expandable member. An inflatable balloon or the like could be used to exert such a force. The expandable member is preferably secured to an outer rim 71 of the occluding member 61 but may also be secured to the frame structure 62 directly or indirectly. The expandable member 65 can be self-expanding from a constrained configuration as can the occluding member 61 and the frame structure 62 and outer rim 71 thereof. The frame structure 62, outer rim 71 and barrier 63 may have construction similar to that described above with regard to the similar elements of the embodiments depicted in FIGS. 1–5.

Figure 7:
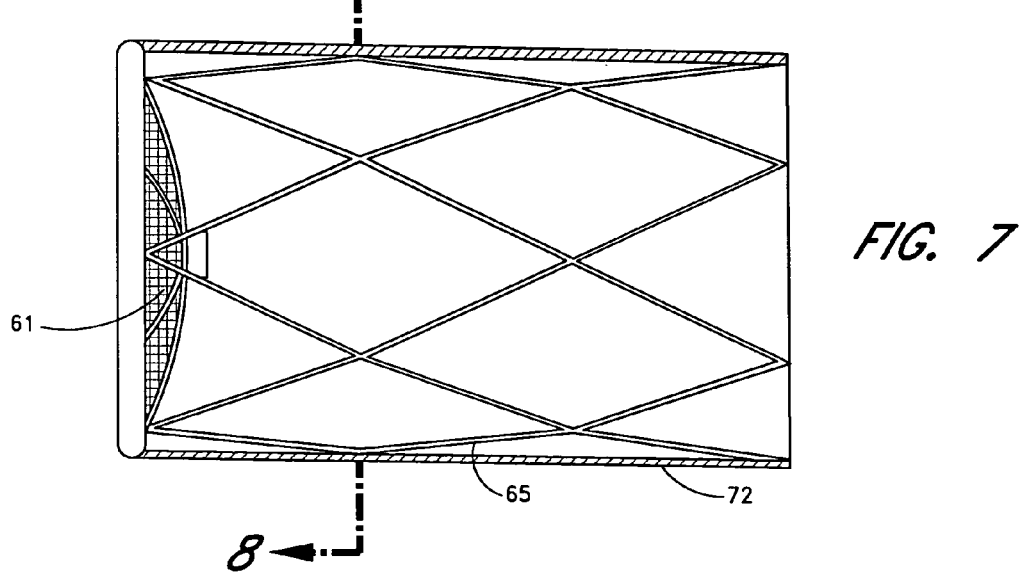
FIG. 7 shows an elevational view in partial section of an apparatus for sealing off a body cavity having features of the invention.

Referring to FIG. 7, the expandable member 65 as shown in FIG. 6 may also have a sheath 72 disposed around it so as to act as a shield between the expandable member and an inner surface of a patient's body cavity or passageway. The sheath 72 may facilitate the sealing function of the occluding member 61, but is primarily intended to prevent damage to either tissue on the inside surface of a body cavity or to the linked elements 66 of the expandable member. The sheath 72 may surround all or part of the expandable member 65 and may be made from a variety of suitable biocompatible materials such as Dacron®, Nylon, TFE, PTFE or ePTFE. The sheath 72 may be a weave, braid, film or have any other suitable configuration. Expandable member 65 may also be coated by dipping, spraying, or other suitable process with a friction reducing material such as Teflon®, or with an active compound such as heparin.

Figure 8:
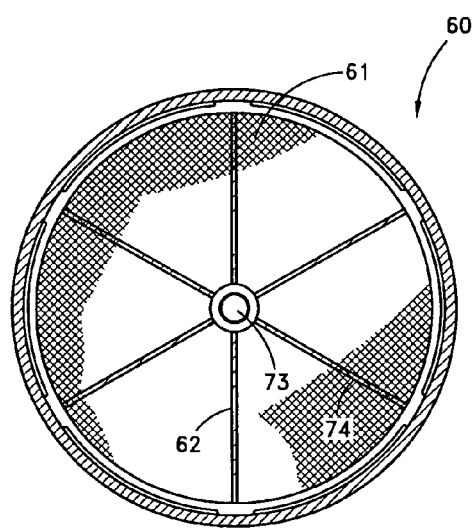
FIG. 8 shows a transverse cross-sectional view of the apparatus of FIG. 7 taken along lines 8—8.

FIG. 8 shows a transverse cross-sectional view of the embodiment of FIG. 7 taken at lines 8—8. The frame structure 62 has an axis or hub 73 disposed at approximately the center of the frame structure which serves to connect the various radial elements 74 of the frame structure. The hub 73 can have an independent structure that links the several elements 74 of the frame structure 62 or it may be merely the terminus of the various frame structure elements and have a solid composition. In either structure, the hub 73 preferably allows a constrained configuration of the occluding member 61 to facilitate percutaneous delivery of the occluding device 60. The hub 73 may also have a lumen disposed therein to allow passage of a guidewire of other guiding member. Preferably, the lumen would have a self sealing valve or gasket which prevents the passage of fluid or embolic material once the guidewire or guiding member is removed from the lumen.

Figure 9:
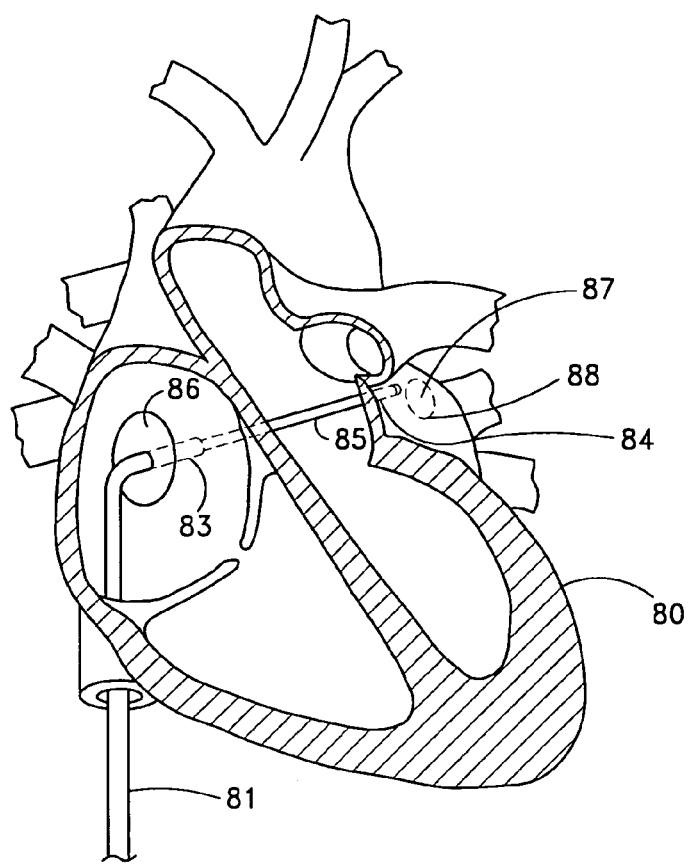
FIG. 9 shows a schematic view of a patient's heart with a transeptal catheter deployed through the septum and a delivery catheter and apparatus for sealing off a body cavity disposed therein.
Figure 9:
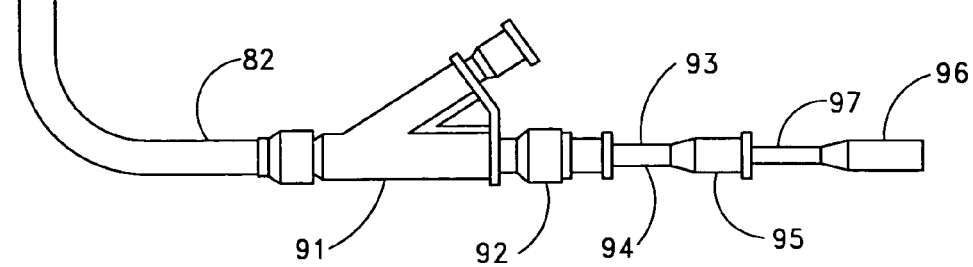

Referring to FIG. 9, a schematic view of a patient's heart 80 in partial section shows a trans-septal catheter 81 having a proximal end 82 and a distal end 83. The distal end 83 of the trans-septal catheter 81 is disposed within a patient's heart 80 with the distal end 84 of a delivery catheter 85 extending from the distal end 83 of the trans-septal catheter. The distal end 83 of the trans-septal catheter 81 has breached the septum 86 of the patient's heart 80 and is disposed adjacent the opening of the patient's LAA 88. At the proximal end 82 of the trans-septal catheter 81 there is a Luer connector 91 coupled to a hemostasis valve 92 which prevents the egress of blood from a lumen 93 of the trans-septal catheter 81. The proximal end 94 of the delivery catheter 85 extends proximally from the hemostasis valve 92 and has a Luer connector 95 attached to the proximal extremity thereof. The proximal end 96 of a plunger 97 extends from the Luer connector 95 of the delivery catheter. The proximal end 94 of the delivery catheter is arranged to allow rotational and axial movement of the plunger 97 while preventing blood or other bodily fluids from leaking between the delivery catheter 85 and the plunger 97.

Figure 10:
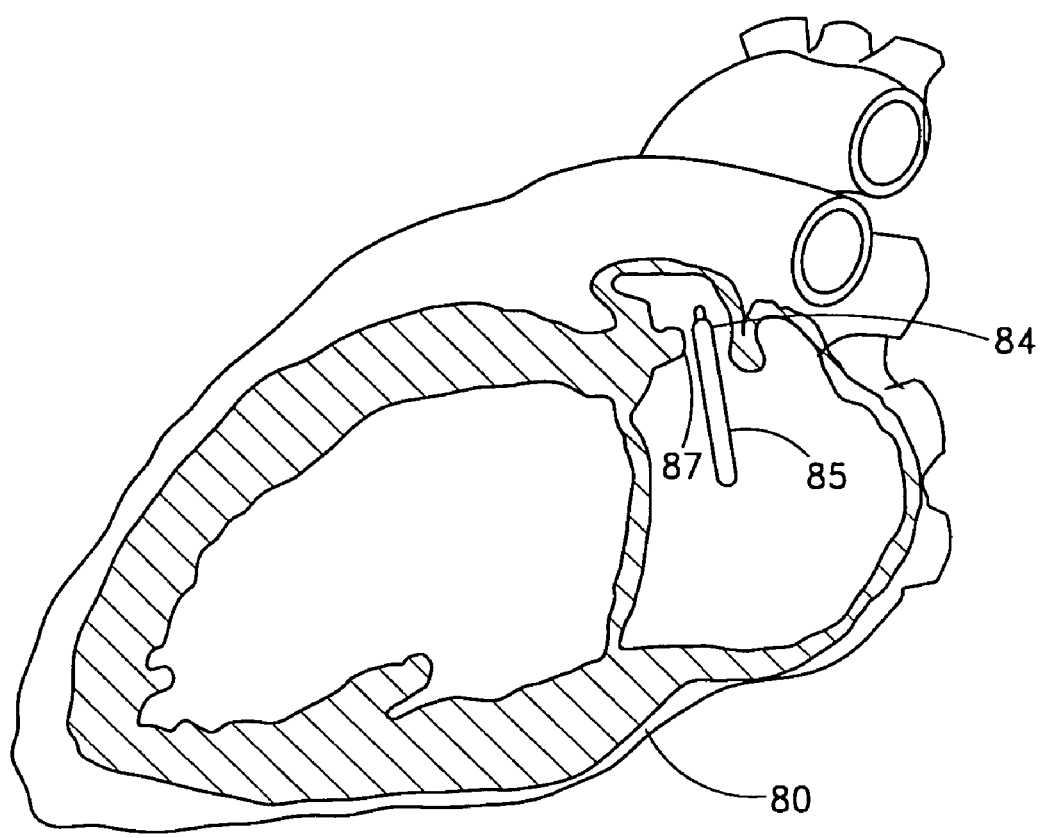
FIG. 10 shows a schematic view of a patient's heart in partial section with a delivery catheter disposed within the opening of the LAA.
Figure 11:
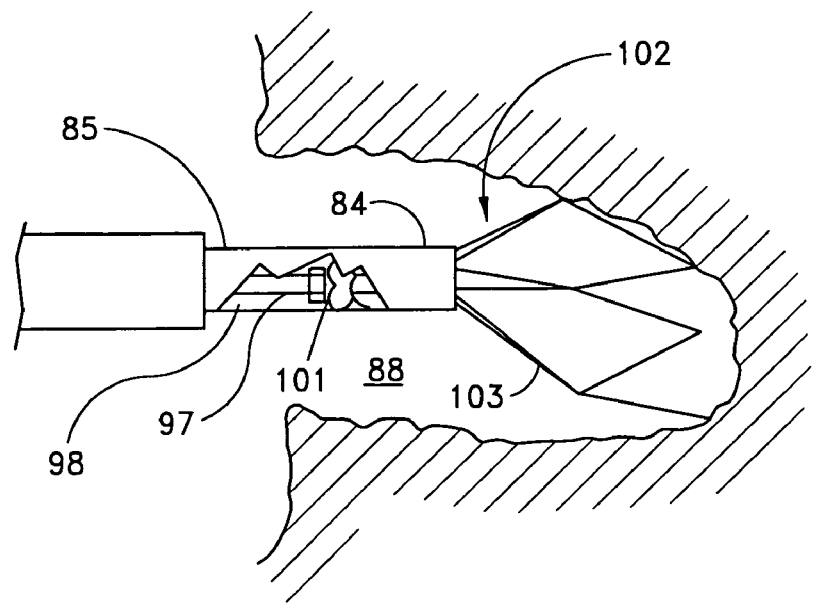
FIG. 11 shows a magnified view of the delivery catheter distal end and the LAA of a patient of FIG. 10 with an apparatus for sealing off a body cavity partially deployed within the LAA.

Referring to FIG. 10, a patient's heart 80 is shown in partial section with the distal end 84 of a delivery catheter 85 disposed within the LAA opening 87. FIG. 11 is a magnified view of the LAA 88 shown in FIG. 10 and the distal end of the delivery catheter 84, which is shown in partial section, contains a plunger 97 which is slideably disposed within an inner lumen 98 of the delivery catheter 85 and serves to apply axial force in a distal direction on the collapsed occluding member 101 disposed within the delivery catheter so as to force the occluding device 102 from the delivery catheter and deploy it. An occluding device 102 having an expandable member 103 and an occluding member 101 secured thereto is partially deployed and extending from the distal end of the delivery catheter 84 into the patient's LAA 88. The occluding device 102 can also be guided into the patient's LAA 88 by use of an appropriate guidewire or guiding member.

Figure 12:
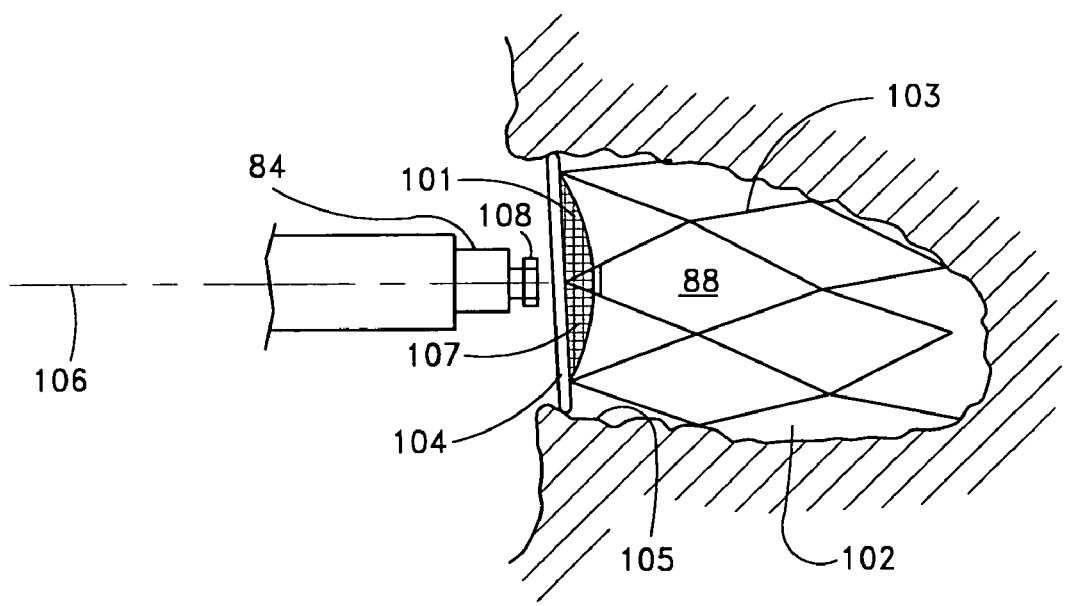
FIG. 12 shows the apparatus for sealing off a body cavity of FIG. 11 fully deployed within a LAA.

FIG. 12 shows the occluding device 102 of FIG. 11 in a deployed state within the patient's LAA 88. An outer rim 104 of the occluding member 101 is in substantial sealing contact with the inside surface 105 of the LAA 88. The expandable member 103 has expanded so as to contact the inside surface 105 of the LAA and secure the occluding device 102 thereto and maintain the occluding member 101 in a substantially perpendicular orientation relative to a longitudinal axis 106 of the LAA 88. A barrier 107 is disposed within an area bounded by the outer rim 104 and is positioned to prevent the passage or embolic or other material to or from the LAA 88. The distal end 108 of the plunger 97 is extending from the distal end of the delivery catheter 84 after having pushed the occluding device 102 from the delivery catheter.

Figure 13:
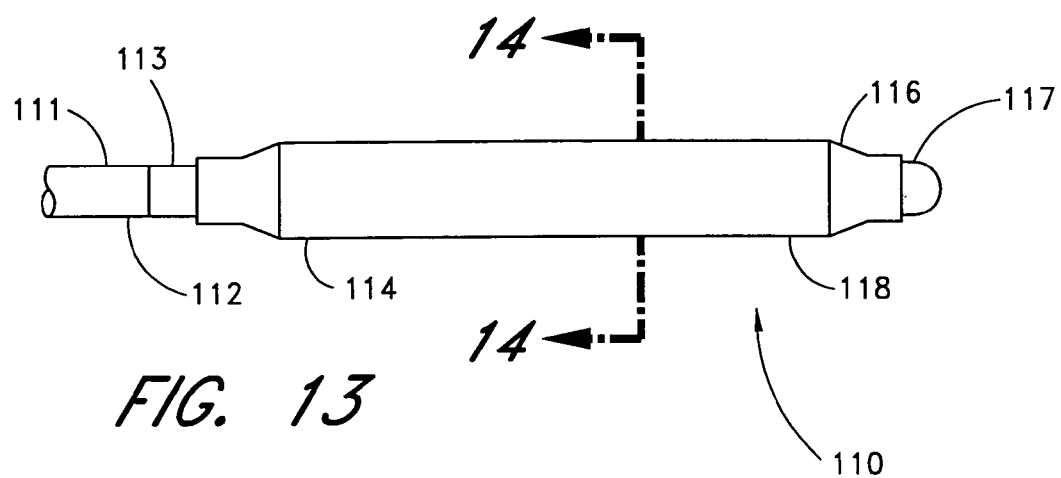
FIG. 13 shows an elevational view of a device for occluding a body cavity having features of the invention.

Referring to FIG. 13, an occluding device 110 having features of the invention is shown. The occluding device 110 has a delivery catheter 111 with a distal end 112, a detachment mechanism 113 disposed on the distal end of the delivery catheter and an occlusive body or inflatable member 114 detachably secured to the detachment mechanism. The inflatable member 114 has a proximal end 115 and a distal end 116 with the proximal end being attached to the detachment mechanism 113 and the distal end terminating at an end cap 117. The inflatable member 114 has an outside surface 118 that may contain a fibrosis inducing material such as Dacron® or other similar materials. The inflatable member 114 may be made from a fluid tight film of polymer material which can be either compliant or non-compliant. Preferably the inflatable member 114 is made from silicone, however, any suitable material such as polyethylene, polyurethane or PET can be used.

The detachment mechanism 113 can be activated by mechanical force or by delivery of thermal or optical energy by a suitable conduit. Alternatively, the inflatable member can be pushed into the LAA from the delivery catheter 111 by an elongate push member without the use of a detachment mechanism. The inflatable member 114 can be filled with a gas, fluid or gel which is injected under pressure through the delivery catheter 114 and into the inflatable member. Suitable fluids to inject would include saline and silicone. The inflatable member 114 may also be filled with a polymer material that can be hardened. Autologus fluid such as blood, or collagen may also be used. A fluid, gel or polymer used to fill the inflatable member may contain contrast agents such as gold, tantalum, bismuth, barium sulfate or the like in order to improve visualization under fluoroscopy or x-ray imaging.

Figure 14:
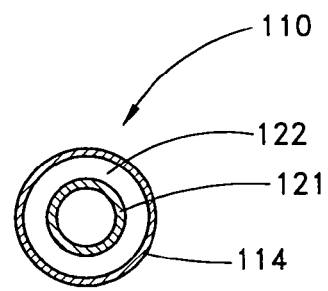
FIG. 14 shows a transverse cross sectional view of the device for occluding a body cavity of FIG. 13 taken along lines 14—14.

FIG. 14 is a transverse cross-sectional view of the occluding device 110 of FIG. 13 taken along lines 14—14. An optional inner shaft 121 is shown disposed within the inflatable member 114, preferably in a concentric arrangement. The inner shaft 121 provides longitudinal axial support to the inflatable member 114 so as to maintain a longitudinal dimension of the inflatable member 114 when it is being inflated and deployed. The inner shaft 121 may be solid or contain one or more lumens that may or may not be in fluid communication with an inner lumen 122 of the inflatable member 114, and can be used for the passage of a guidewire or guiding member.

Figure 15:
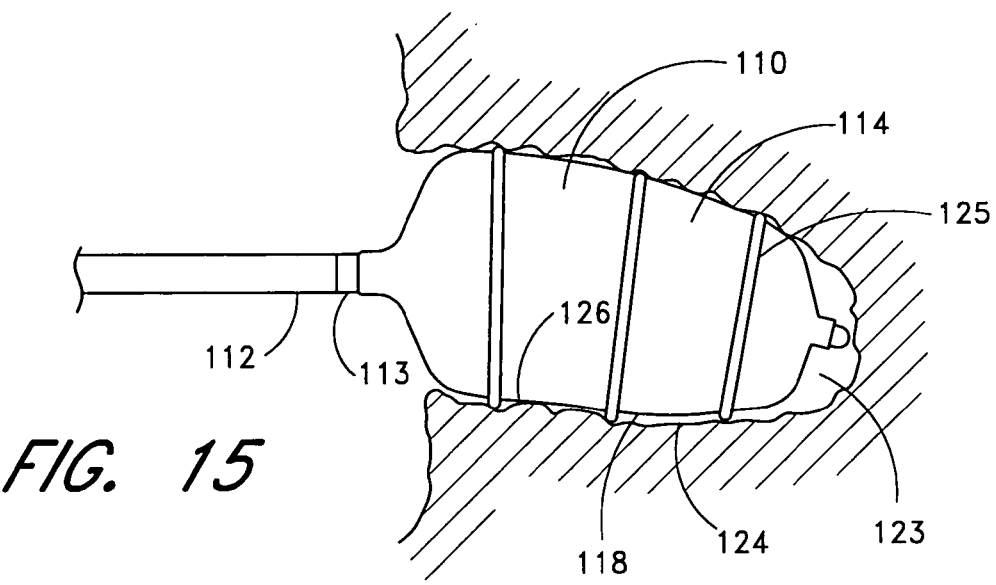
FIG. 15 shows a device for occluding a body cavity having features of the invention deployed within a LAA.

FIG. 15 depicts an alternative embodiment of an occluding device 110 which consists of an inflatable member 114 similar to the inflatable member of FIG. 13, shown substantially deployed, within a patient's LAA 123. The inflatable member 114 has been at least partially filled with a fluid, gas or gel within the patient's LAA 123 such that the outside surface of the inflatable member 118 is in contact with at least part of the inside surface 124 of the LAA. The inflatable member 114 can have rib members 125 which can mechanically interlock with the trebeculae 126 of the inside surface of the LAA 124 or other surface irregularities of the inside surface of a patient's body cavity or passageway. The rib members 125 form a complete circumference of the inflatable member 114, but could also form a partial circumference, spiral configuration, or consist of random projections on the surface of the inflatable member 118. The rib members 125 should extend radially about 1 to about 4 mm from the nominal surface of the inflatable member 114, and are preferably spaced about 3 to about 8 mm from each other. The rib members 125 may be made from any suitable polymer material, but are preferably made from the same material as the inflatable member, and are integrally molded thereon, or bonded thereto with a heat weld or adhesive bond suitable for bonding flexibly medical polymers. The inflatable member 114 is depicted with the distal end of the delivery catheter 112 and detachment mechanism 113 attached. As an alternative, or in addition to the polymer rib members 125 shown in FIG. 15, barbs or hooks could be secured to the outside surface of the inflatable member 114 which are configured to engage the inside surface of a patient's LAA 124. Preferably, barbs or hooks disposed on the outside surface of the inflatable member and configured to engage the tissue of the inside surface of a patient's LAA 124 would have a proximally directed bias at their radial extremity so that the barbs would fold down and move easily in a distal direction during insertion of the inflatable member 114, but would spring outward and aggressively engage the tissue of the body cavity upon movement in a proximal direction of the inflatable member.

Figure 16:
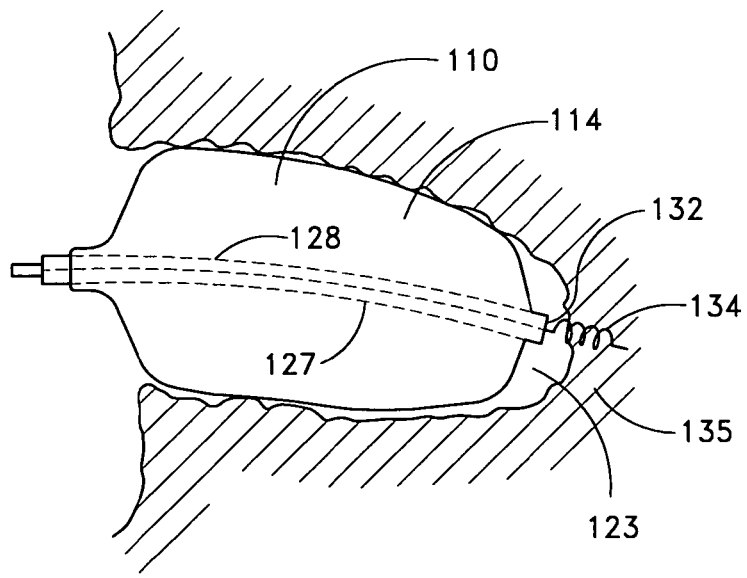
FIG. 16 shows a device for occluding a body cavity having features of the invention deployed within a LAA.

FIG. 16 depicts an occluding device 110 consisting of an inflatable member 114 which is shown deployed within a patient's LAA 123. The embodiment of the inflatable member 114 shown in FIG. 16 has an optional retention member 127 with a tissue penetrating shaft 128 which has a proximal 131 end and a distal end 132. A rotational coupling 133 is disposed at the proximal end 131 of the tissue penetrating shaft 128 and a helically shaped extremity 134 is disposed at the distal end of the shaft 132. The helically shaped distal extremity 134 is shown deployed within and mechanically engaging wall tissue 135 of the LAA so as to secure the inflatable member 114 and maintain its position within the LAA 123 of the patient.

Figure 17:
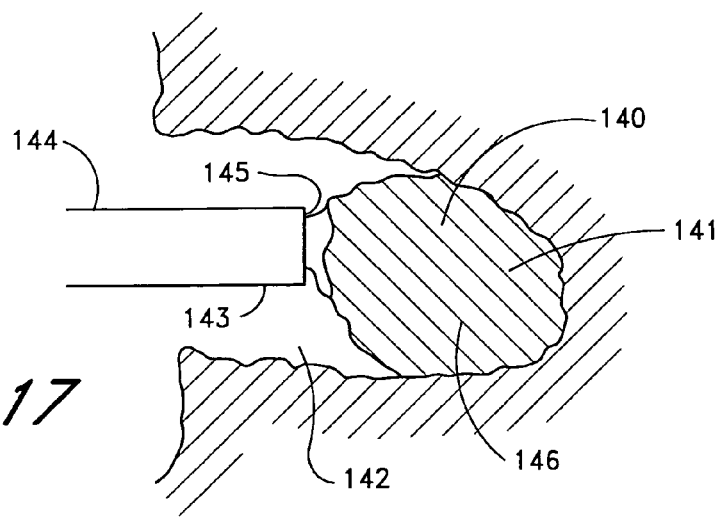
FIG. 17 shows a LAA being occluded by a method having features of the invention.

FIG. 17 shows an alternative embodiment of an occlusive member 140 consisting of a polymer mass 141 which has been injected or delivered into a patient's LAA 142. The distal end 143 of a delivery catheter 144 has a lumen 145 therein which extends to a proximal end of the delivery catheter which is in fluid communication with a source of pressurized polymer material. A source of pressurized polymer material 146 can be any type of pump or device capable of forcing a polymer fluid or gel into the proximal end of the delivery catheter with sufficient pressure to force the polymer fluid or gel out the distal end 143 of the delivery catheter 144 and into a patient's body cavity or passageway. The delivery catheter 144 may be positioned by the techniques discussed above, e.g., the Mullins trans-septal approach or any other suitable method. Once the distal end of the delivery catheter 143 is disposed within a desired portion of the patient's LAA 142, the polymer mass 141 may be injected to fill the cavity to the desired level. The LAA 142 can be completely or partially filled with the polymer mass 141 which can be formulated to harden over time, with heat or remain in a fluid or gel state. The distal end of the delivery catheter can optionally include an expandable member which is used to substantially seal the delivery catheter against the inside surface of the opening of the patient's body cavity during the delivery of polymer material. The expandable member can be an inflatable balloon or the like which are well known in the art.

Optionally, a retention member 127 having a tissue penetrating shaft 128 or the like, such as shown in FIG. 16 with regard to the inflatable member 114, may be deployed within the LAA 142 prior to injection of the polymer mass 141 and captured thereby so as to secure the polymer mass within the LAA. Alternatively, the polymer mass can be used to fill the patient's LAA and surround and secure a deployed device as shown in FIG. 4 or 5 in the patient's LAA 142.

Figure 18:
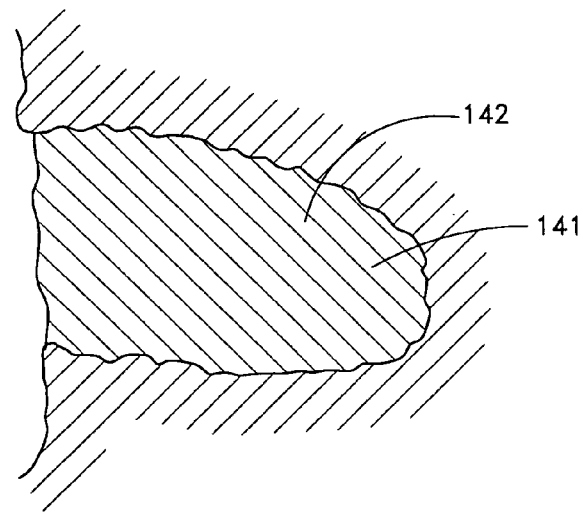
FIG. 18 shows a LAA occluded by method having features of the invention.

Once a desired amount of polymer mass 141 has been injected into the LAA 142, as assessed for example by TE Echo imaging, the delivery catheter 144 may be withdrawn and the procedure terminated. Preferably, the entire LAA 142 of a patient is filled with the polymer mass 141 as shown in FIG. 18 and hardens or gels to maintain its shape. It may be desirable to have the polymer mass 141 retain a soft compressible form after setting or hardening so that it is at least partially compliant with the constrictive pumping action of a heart and resistant to fatigue as a result thereof.

A material used to form the polymer mass 141 may contain contrast agents such as gold, platinum, tantalum, bismuth or the like in order to better visualize the deployment of the polymer mass under fluoroscopic or x-ray imaging.

Figure 19:
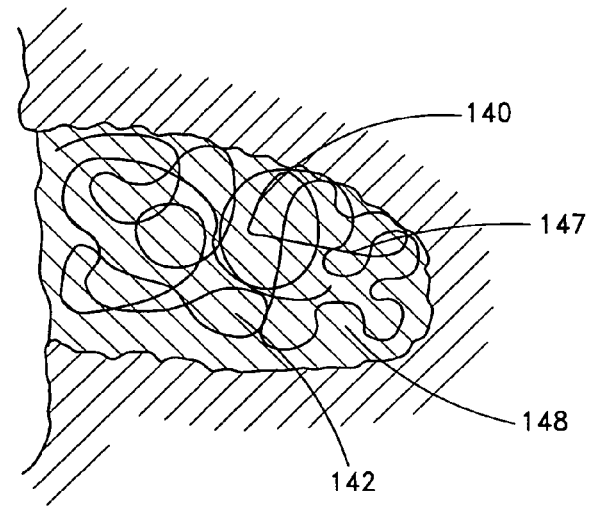
FIG. 19 shows a LAA occluded by method having features of the invention.

Another alternative embodiment of an occlusive member 140 can be found in FIG. 19 which shows an occlusive coil 147 which has been deployed within an LAA 142. The occlusive coil 147 as shown has assumed a random configuration that is mechanically occluding the LAA 142 and which has induced clot and/or fibrosis formation 148 which further facilitates occlusion of the LAA 142.

Figure 20:
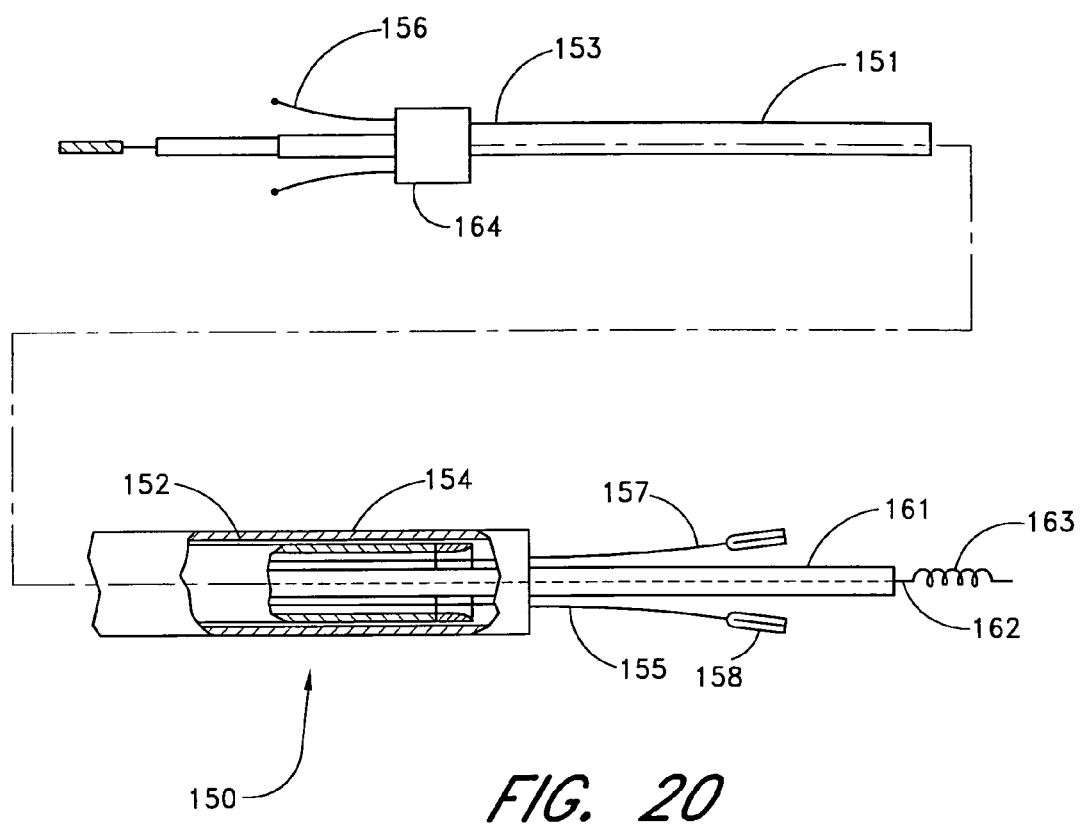
FIG. 20 is an elevational view of an apparatus for closing an interior body cavity of a patient in partial section having features of the invention.

An apparatus for closing off a body cavity or passageway 150 is shown in FIG. 20 which has features of the present invention. The apparatus 150 has an elongate shaft 151 with an inner lumen 152 and a proximal end 153 and a distal end 154. Slideably disposed within the inner lumen 152 of the elongate shaft 151 are at least two elongate members 155 which have proximal ends 156 and distal ends 157 and have tissue attachment members 158 disposed on the distal ends. An optional distal anchor member 161 is also slideably disposed within the inner lumen 152 of the elongate shaft 151 and preferably has a distal end 162 terminating with a helical member 163. The proximal end 153 of the elongate shaft 151 has a proximal control module 164 which seals the inner lumen 152 of the elongate shaft 151 and allows rotation and translation of the proximal ends 156 of the elongate members 155 and the distal anchor member 161 while maintaining a seal between said members to prevent leakage of bodily fluids therefrom. The proximal control module 164 can optionally be configured to control advancement and retraction of the elongate members 155 and control activation of the tissue attachment members 158.

Figure 21:
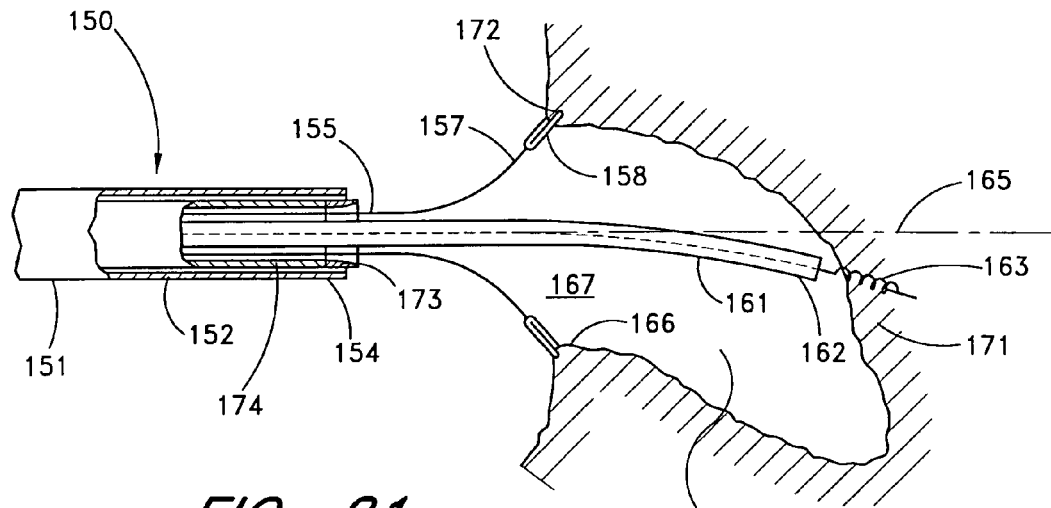
FIG. 21 is a schematic view of an apparatus for closing an interior body cavity of a patient in contact with tissue of a LAA.
Figure 22:
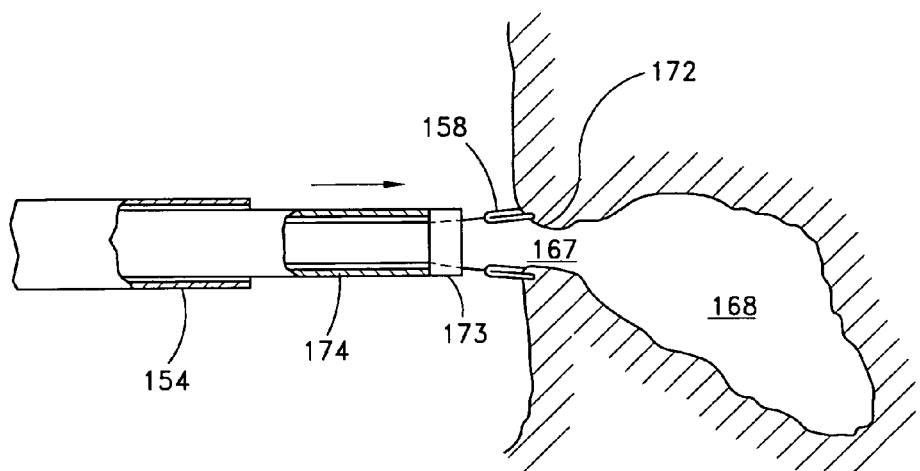
FIG. 22 is a schematic view of an apparatus for closing an interior body cavity of a patient in contact with tissue of a LAA.
Figure 23:
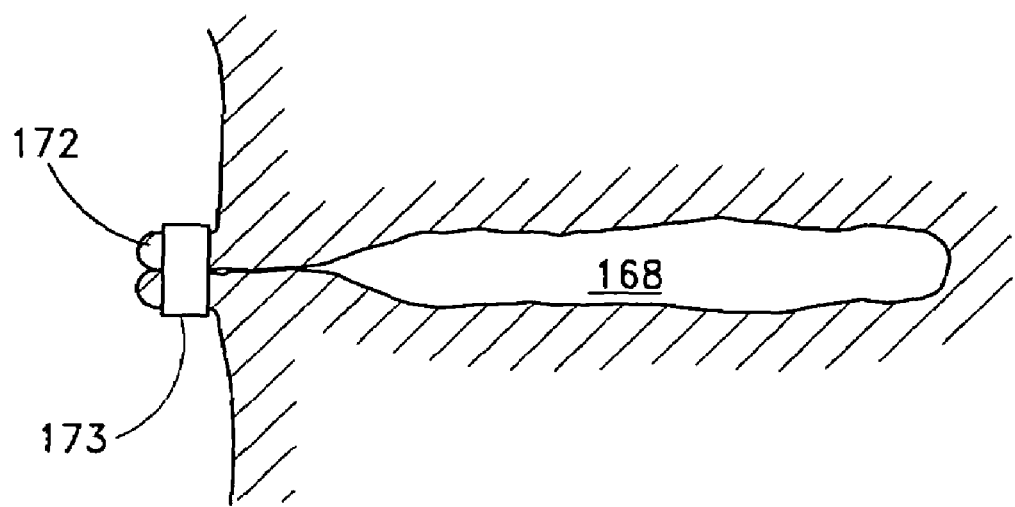
FIG. 23 shows a LAA which has been closed by a method having features of the invention.

FIG. 21 shows the apparatus for closing off a body cavity 150 of FIG. 20 with the distal ends of the elongate members 157 and the tissue attachment members 158 extending distally from the distal end of the elongate shaft 154. The distal ends of the elongate members 157 are angled or deflected from a longitudinal axis 165 of the elongate shaft 151 so as to engage tissue 166 of the opening 167 of the LAA 168 as shown. The elongate members 155 may be deflected by an abutment or angulation contained in the distal end of the elongate shaft 154, but are preferably preshaped in an angled configuration which manifests when the distal ends are freed of the constraint of the inner lumen 152 of the elongate shaft an allowed to assume their relaxed preshaped condition. The helical member 163 at the distal end 162 of the distal anchor member 161 is engaged with the wall tissue 171 of the LAA 168 so as to provide an optional anchor that can be used to move the elongate shaft 151 relative to the distal anchor member 161 and give greater control of the longitudinal axial movement of the elongate shaft relative to the LAA opening 167. The tissue attachment members 158 are shown attached to the annular edge 172 of the LAA opening 167. Once the tissue attachment members 158 are attached, a closure member or retaining ring 173 may be advanced distally by applying axial force on an elongate push shaft 174 which draws the tissue attachment members 158 and the tissue attached thereto closer together as shown in FIG. 22. As the closure member 173 is further advanced distally, the annular edge of the LAA 172 is drawn closed, and eventually, the annular edge of the LAA will be completely closed into a closed state with the closure member 173 surrounding and compressing the tissue of the annular edge as shown in FIG. 23. Once a closed state of the LAA is achieved, the tissue attachment members 158 may be detached, and the apparatus for closing off a body cavity 150 withdrawn. One alternative method can have the tissue attachment members 158 drawn together by retracting them proximally into the distal end 154 of the elongate shaft 151 as opposed to distally advancing the closure member 173 with the elongate push shaft 174. In this way, the annular edge of the LAA 172 can be drawn into a closed state within the distal end 154 of the elongate shaft 151 at which point the annular edge may be fixed in the closed state by a variety of methods including suturing, tissue welding, the application of a suitable biocompatible adhesive, surgical staples or the like.

Figure 24:
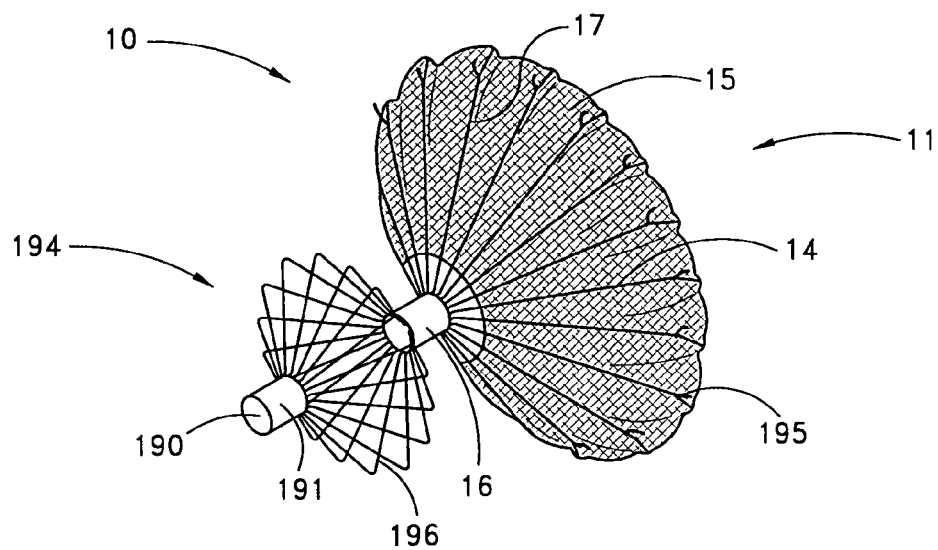
FIG. 24 is a perspective view of an occlusion device in accordance with the present invention.
Figure 25:
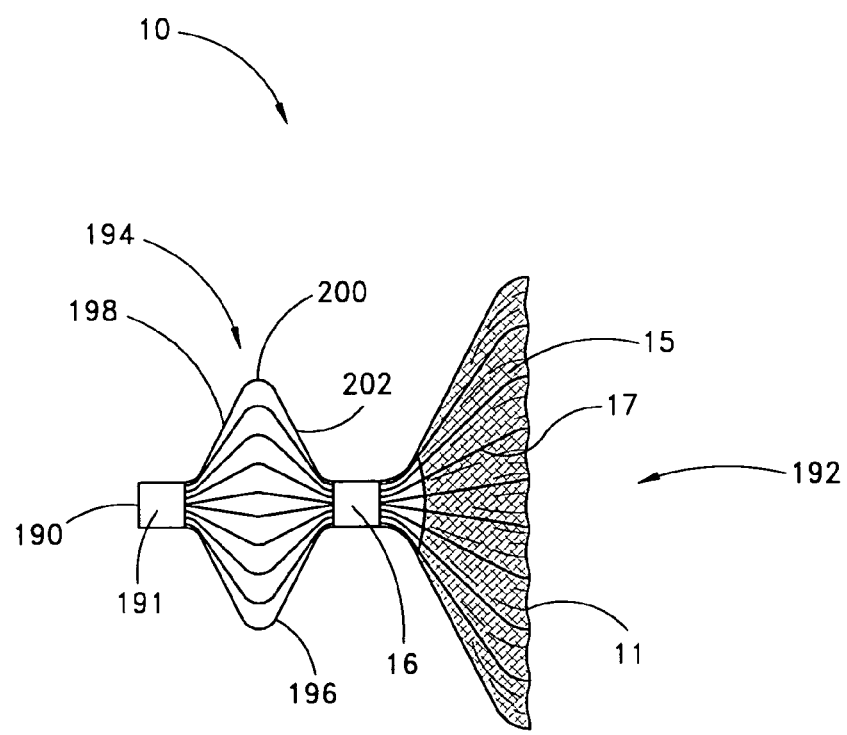
FIG. 25 is a side elevational view of the occlusion device shown in FIG. 24.

Referring to FIGS. 24 and 25, there is illustrated an alternate embodiment of the occlusion device 10 in accordance with the present invention. The occlusion device 10 comprises an occluding member 11 comprising a frame 14 and a barrier 15. In the illustrated embodiment, the frame 14 comprises a plurality of radially outwardly extending spokes 17 each having a length within the range of from about 0.5 cm to about 2 cm from a hub 16. In one embodiment, the spokes have an axial length of about 1.5 cm. Depending upon the desired introduction crossing profile of the collapsed occlusion device 10, as well as structural strength requirements in the deployed device, anywhere within the range of from about 3 spokes to about 40 spokes may be utilized. In some embodiments, anywhere from about 12 to about 24 spokes are utilized, and, 18 spokes are utilized in one embodiment.

The spokes are advanceable from a generally axially extending orientation such as to fit within a tubular introduction catheter to a radially inclined orientation as illustrated in FIG. 24 and FIG. 25 following deployment from the catheter. In a self-expandable embodiment, the spokes are biased radially outwardly such that the occlusion member expands to its enlarged, implantation cross-section under its own bias following deployment from the catheter. Alternatively, the occlusion member may be enlarged using any of a variety of enlargement structures such as an inflatable balloon.

Preferably, the spokes comprise a metal such as stainless steel, Nitinol, Elgiloy, or others which can be determined through routine experimentation by those of skill in the art. Wires having a circular or rectangular cross-section may be utilized depending upon the manufacturing technique. In one embodiment, rectangular cross section spokes are cut such as by known laser cutting techniques from tube stock, a portion of which forms the hub 16.

The barrier 15 may comprise any of a variety of materials which facilitate cellular in-growth, such as ePTFE. The suitability of alternate materials for barrier 15 can be determined through routine experimentation by those of skill in the art. The barrier 15 may be provided on either one or both sides of the occlusion member. In one embodiment, the barrier 15 comprises two layers, with one layer on each side of the frame 14. The two layers may be bonded to each other around the spokes 17 in any of a variety of ways, such as by heat bonding with or without an intermediate bonding layer such as polyethylene or FEP, adhesives, sutures, and other techniques which will be apparent to those of skill in the art in view of the disclosure herein. The barrier 15 preferably has a thickness of no more than about 0.003" and a porosity within the range of from about 5 µm to about 601 µm.

The barrier 15 in one embodiment preferably is securely attached to the frame 14 and retains a sufficient porosity to facilitate cellular ingrowth and/or attachment. One method of manufacturing a suitable composite membrane barrier 15 is illustrated in FIGS. 36–39. As illustrated schematically in FIG. 36, a bonding layer 254 preferably comprises a mesh or other porous structure having an open surface area within the range of from about 10% to about 90%. Preferably, the open surface area of the mesh is within the range of from about 30% to about 60%. The opening or pore size of the bonding layer 254 is preferably within the range of from about 0.005 inches to about 0.050 inches, and, in one embodiment, is about 0.020 inches. The thickness of the bonding layer 254 can be varied widely, and is generally within the range of from about 0.0005 inches to about 0.005 inches. In a preferred embodiment, the bonding layer 254 has a thickness of about 0.001 to about 0.002 inches. One suitable polyethylene bonding mesh is available from Smith and Nephew, under the code SN9.

Referring to FIG. 37, the bonding layer 254 is preferably placed adjacent one or both sides of a spoke or other frame element 14. The bonding layer 254 and frame 14 layers are then positioned in-between a first membrane 250 and a second membrane 252 to provide a composite membrane stack. The first membrane 250 and second 252 may comprise any of a variety of materials and thicknesses, depending upon the desired functional result. Generally, the membrane has a thickness within the range of from about 0.0005 inches to about 0.010 inches. In one embodiment, the membranes 250 and 252 each have a thickness on the order of from about 0.001 inches to about 0.002 inches, and comprise porous ePTFE, having a porosity within the range of from about 10 microns to about 100 microns.

The composite stack is heated to a temperature of from about 200° to about 300°, for about 1 minute to about 5 minutes under pressure to provide a finished composite membrane assembly with an embedded frame 14 as illustrated schematically in FIG. 38. The final composite membrane has a thickness within the range of from about 0.001 inches to about 0.010 inches, and, preferably, is about 0.002 to about 0.003 inches in thickness. However, the thicknesses and process parameters of the foregoing may be varied considerably, depending upon the materials of the bonding layer 254 the first layer 250 and the second layer 252.

As illustrated in top plan view in FIG. 39, the resulting finished composite membrane has a plurality of "unbonded" windows or areas 256 suitable for cellular attachment and/or ingrowth. The attachment areas 256 are bounded by the frame 14 struts, and the cross-hatch pattern formed by the bonding layer 254. In the illustrated embodiment, the filaments of the bonding layer 254 are oriented in a nonparallel relationship with the struts of frame 14, and, in particular, at an angle within the range of from about 15° to about 85° from the longitudinal axis of the struts. Preferably, a regular window 256 pattern is produced.

The foregoing procedure allows the bonding mesh to flow into the first and second membranes 250 and 252 and gives the composite membrane 15 greater strength (both tensile and tear strength) than the components without the bonding mesh. The composite allows uniform bonding while maintaining porosity of the membrane 15, to facilitate tissue attachment. By flowing the thermoplastic bonding layer into the pores of the outer mesh layers 250 and 252, the composite flexibility is preserved and the overall composite layer thickness can be minimized.

The occlusion device 10 may be further provided with a bulking element or stabilizer 194. The stabilizer 194 may be spaced apart along an axis from the occluding member 11. In the illustrated embodiment, a distal end 190 and a proximal end 192 are identified for reference. The designation proximal or distal is not intended to indicate any particular anatomical orientation or deployment orientation within the deployment catheter. As shown in FIGS. 24 and 25, the stabilizer 194 is spaced distally apart from the occluding member 11.

For use in the LAA, the occluding member 11 has an expanded diameter within the range of from about 1 cm to about 5 cm, and, in one embodiment, about 3 cm. The axial length of the occluding member 11 in an expanded, unstressed orientation from the distal end 192 to the proximal hub 16 is on the order of about 1 cm. The overall length of the occlusion device 10 from the distal end 192 to the proximal end 190 is within the range of from about 1.5 cm to about 4 cm and, in one embodiment, about 2.5 cm. The axial length of the stabilizer 194 between distal hub 191 and proximal hub 16 is within the range of from about 0.5 cm to about 2 cm, and, in one embodiment, about 1 cm. The expanded diameter of the stabilizer 194 is within the range of from about 0.5 cm to about 2.5 cm, and, in one embodiment, about 1.4 cm. The outside diameter of the distal hub 191 and proximal hub 16 is about 2.5 mm.

Preferably, the occlusion device 10 is provided with one or more retention structures for retaining the device in the left atrial appendage or other body lumen. In the illustrated embodiment, a plurality of barbs or other anchors 195 are provided, for engaging adjacent tissue to retain the occlusion device 10 in its implanted position and to limit relative movement between the tissue and the occlusion device. The illustrated anchors are provided on one or more of the spokes 17, or other portion of frame 14. Preferably, every spoke, every second spoke or every third spoke are provided with one or two anchors each. The illustrated anchor is in the form of a barb, for extending into tissue at or near the opening of the LAA.

One or more anchors 195 may also be provided on the stabilizer 194, such that it assists not only in orienting the occlusion device 10 and resisting compression of the LAA, but also in retaining the occlusion device 10 within the LAA. Any of a wide variety of structures may be utilized for anchor 195, either on the occluding member 11 or the stabilizer 194 or both, such as hooks, barbs, pins, sutures, adhesives and others which will be apparent to those of skill in the art in view of the disclosure herein.

In use, the occlusion device 10 is preferably positioned within a tubular anatomical structure to be occluded such as the left atrial appendage such that the occluding member 11 is positioned across or near the opening to the LAA and the stabilizer 194 is positioned within the LAA. The stabilizer 194 assists in the proper location and orientation of the occluding member 11, as well as resists compression of the LAA behind the occluding member 11. The present inventors have determined that following deployment of an occluding member 11 without a stabilizer 194 or other bulking structure to resist compression of the LAA, normal operation of the heart may cause compression and resulting volume changes in the LAA, thereby forcing fluid past the occluding member 11 and inhibiting or preventing a complete seal. Provision of a stabilizer 194 dimensioned to prevent the collapse or pumping of the LAA thus minimize leakage, and provision of the barbs facilitates endothelialization or other cell growth across the occluding member 11.

For this purpose, the stabilizer 194 is preferably movable between a reduced cross-sectional profile for transluminal advancement into the left atrial appendage, and an enlarged cross-sectional orientation as illustrated to fill or to substantially fill a cross-section through the LAA. The stabilizing member may enlarge to a greater cross section than the anatomical cavity, to ensure a tight fit and minimize the likelihood of compression. One convenient construction includes a plurality of elements 196 which are radially outwardly expandable in response to axial compression of a distal hub 191 towards a proximal hub 16. Elements 196 each comprise a distal segment 198 and a proximal segment 202 connected by a bend 200. The elements 196 may be provided with a bias in the direction of the radially enlarged orientation as illustrated in FIG. 25, or may be radially expanded by applying an expansion force such as an axially compressive force between distal hub 191 and proximal hub 16 or a radial expansion force such as might be applied by an inflatable balloon. Elements 196 may conveniently be formed by laser cutting the same tube stock as utilized to construct the distal hub 191, proximal hub 16 and frame 14, as will be apparent to those of skill in the art in view of the disclosure herein. Alternatively, the various components of the occlusion device 10 may be separately fabricated or fabricated in subassemblies and secured together during manufacturing.

As a post implantation step for any of the occlusion devices disclosed herein, a radiopaque dye or other visualizable media may be introduced on one side or the other of the occlusion device, to permit visualization of any escaped blood or other fluid past the occlusion device. For example, in the context of a left atrial appendage application, the occlusion device may be provided with a capillary tube or aperture which permit introduction of a visualizable dye from the deployment catheter through the occlusion device and into the entrapped space on the distal side of the occlusion device. Alternatively, dye may be introduced into the entrapped space distal to the occlusion device such as by advancing a small gauge needle from the deployment catheter through the barrier 15 on the occlusion device, to introduce dye.

Figure 26:
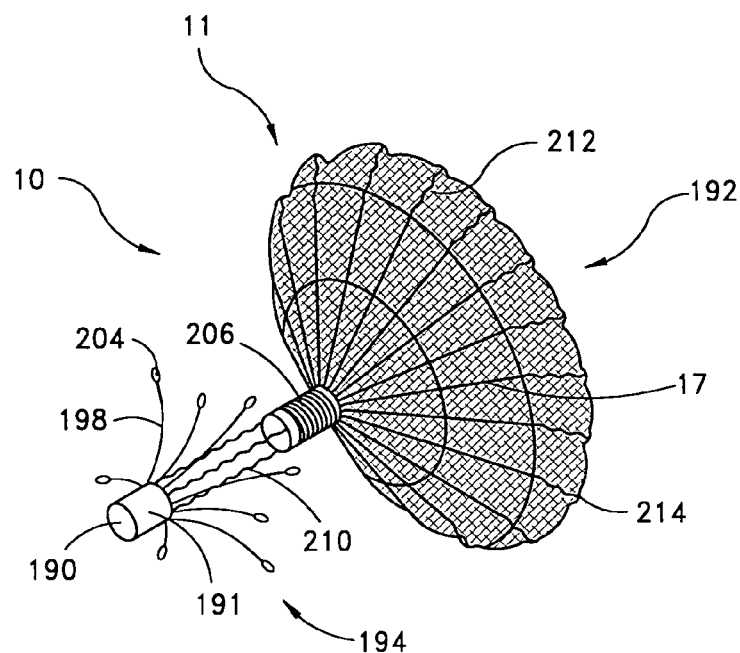
FIG. 26 is a perspective view of an alternate embodiment of the present invention.
Figure 27:
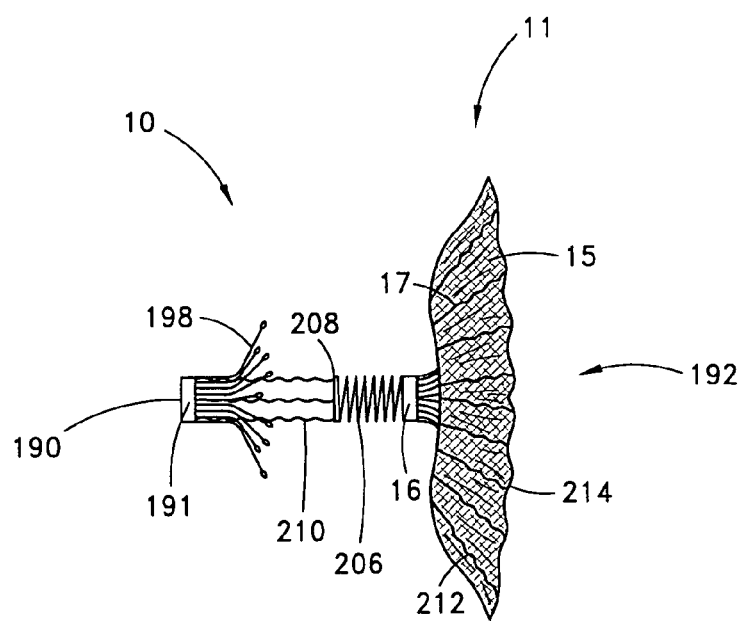
FIG. 27 is a side elevational view of the embodiment shown in FIG. 26.

A further embodiment of the occlusion device 10 is illustrated in FIGS. 26–27. The occlusion device 10 comprises an occlusion member 11 and a stabilizing member 194 as in the previous embodiment. In the present embodiment, however, each of the distal segments 198 inclines radially outwardly in the proximal direction and terminates in a proximal end 204. The proximal end 204 may be provided with atraumatic configuration, for pressing against, but not penetrating, the wall of the left atrial appendage or other tubular body structure. Three or more distal segments 198 are preferably provided, and generally anywhere within the range of from about 6 to about 20 distal segments 198 may be used. In one embodiment, 9 distal segments 198 are provided. In this embodiment, 3 of the distal segments 198 have an axial length of about 5 mm, and 6 of the distal segments 198 have an axial length of about 1 cm. Staggering the lengths of the proximal segments 198 may axially elongate the zone in the left atrial appendage against which the proximal ends 204 provide anchoring support for the occlusion device.

The occlusion device 10 illustrated in FIGS. 26 and 27 is additionally provided with a hinge 206 to allow the longitudinal axis of the occlusion member 11 to be angularly oriented with respect to the longitudinal axis of the stabilizing member 194. In the illustrated embodiment, the hinge 206 is a helical coil, although any of a variety of hinge structures can be utilized. The illustrated embodiment may be conveniently formed by laser cutting a helical slot through a section of the tube from which the principal structural components of the occlusion device 10 are formed. At the distal end of the hinge 206, an annular band 208 connects the hinge 206 to a plurality of axially extending struts 210. In the illustrated embodiment 210, three axial struts 210 are provided, spaced equilaterally around the circumference of the body. Axial struts 210 may be formed from a portion of the wall of the original tube stock, which portion is left in its original axial orientation following formation of the distal segments 198 such as by laser cutting from the tubular wall.

The occlusion member 11 is provided with a proximal zone 212 on each of the spokes 17. Proximal zone 212 has an enhanced degree of flexibility, to accommodate the fit between the occlusion member 11 and the wall of the left atrial appendage. Proximal section 212 may be formed by reducing the cross sectional area of each of the spokes 17, or by increasing the length of each spoke by making a wave pattern as illustrated.

Each of the spokes 17 terminates in a proximal point 214. Proximal point 214 may be contained within layers of the barrier 15, or may extend through or beyond the barrier 15 such as to engage adjacent tissue and assist in retaining the occlusion device 10 at the deployment site.

Figure 28:
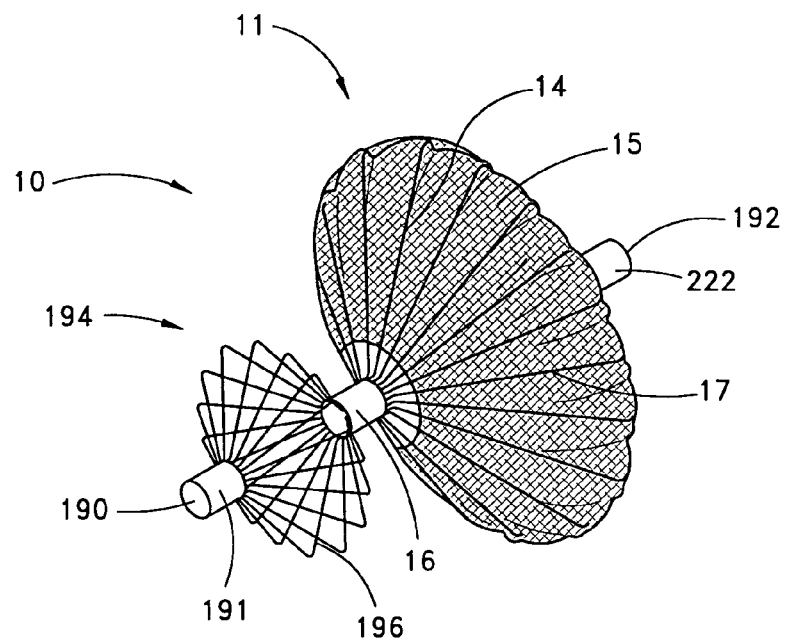
FIG. 28 is a perspective view of a further embodiment of the present invention.
Figure 29:
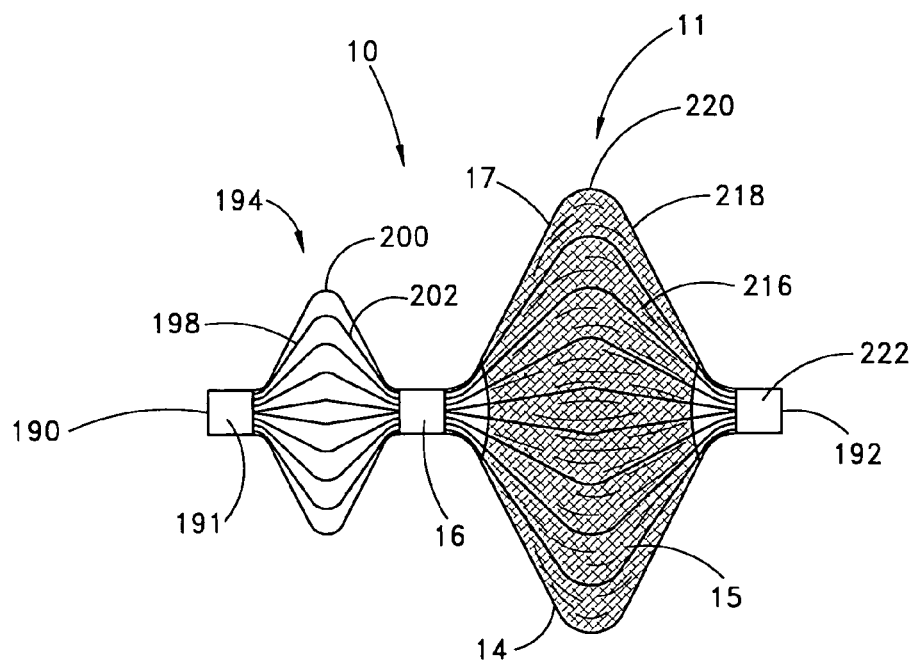
FIG. 29 is a side elevational view of the embodiment of FIG. 28.
Figure 31:
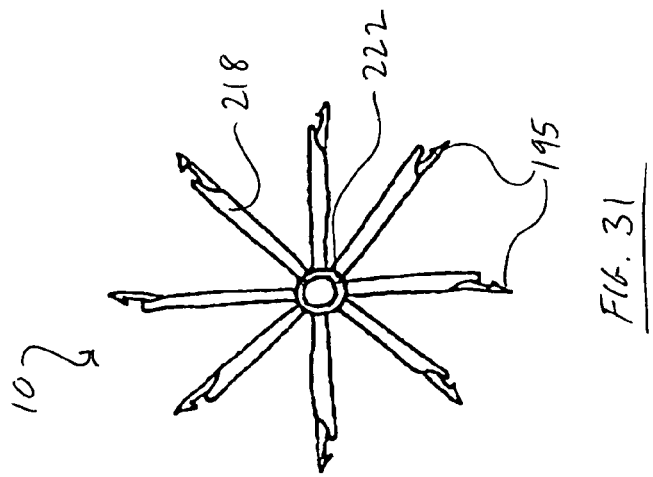
FIG. 31 is an end view taken along the line 31—31 of FIG. 30.

Referring to FIGS. 28 and 29, a further variation on the occlusion device 10 illustrated in FIGS. 24 and 25 is provided. The occlusion device 10 is provided with a proximal face 216 on the occlusion member 11, instead of the open and proximally concave face on the embodiment of FIGS. 24 and 25. The proximal face 216 is formed by providing a proximal spoke 218 which connects at an apex 220 to each distal spoke 17. Proximal spokes 218 are each attached to a hub 222 at the proximal end 192 of the occlusion device 10. The barrier 15 may surround either the proximal face or the distal face or both on the occlusion member 11. In general, provision of a proximal spoke 218 connected by an apex 220 to a distal spoke 17 provides a greater radial force than a distal spoke 17 alone, which will provide an increased resistance to compression if the occlusion member 11 is positioned with the LAA.

Referring to FIGS. 30–35, an alternate embodiment of the occlusion device in accordance with the present invention is illustrated. In general, the occlusion device 10 comprises an occluding member but does not include a distinct stabilizing member as has been illustrated in connection with previous embodiments. Any of the embodiments previously disclosed herein may also be constructed using the occluding member only, and omitting the stabilizing member as will be apparent to those of skill in the art in view of the disclosure herein.

The occluding device 10 comprises a proximal end 192, a distal end 190, and a longitudinal axis extending therebetween. A plurality of supports 228 extend between a proximal hub 222 and a distal hub 191. At least two or three supports 228 are provided, and preferably at least about six. In one embodiment, eight supports 228 are provided. However, the precise number of supports 228 can be modified, depending upon the desired physical properties of the occlusion device 10 as will be apparent to those of skill in the art in view of the disclosure herein, without departing from the present invention.

Each support 228 comprises a proximal spoke portion 218, a distal spoke portion 217, and an apex 220 as has been discussed. However, each of the proximal spoke 218, distal spoke 17 and apex 220 may be a region on an integral support 228, such as a continuous rib or frame member which extends in a generally curved configuration as illustrated with a concavity facing towards the longitudinal axis of the occlusion device 10. Thus, no distinct point or hinge at apex 220 is necessarily provided as is disclosed in previous embodiments, which include a hinged connection between proximal spoke 218 and distal spoke 17.

At least some of the supports 228, and, preferably, each support 228, is provided with one or two or more barbs 195.

In the illustrated configuration, the occlusion device 10 is in its enlarged orientation, such as for occluding a left atrial appendage or other body cavity or lumen. In this orientation, each of the barbs 195 projects generally radially outwardly from the longitudinal axis, and are inclined in the proximal direction. In an embodiment where the barbs 195 and corresponding support 228 are cut from a single ribbon, sheet or tube stock, the barb 195 will incline radially outwardly at approximately a tangent to the curve formed by the support 228.

Figure 30A:
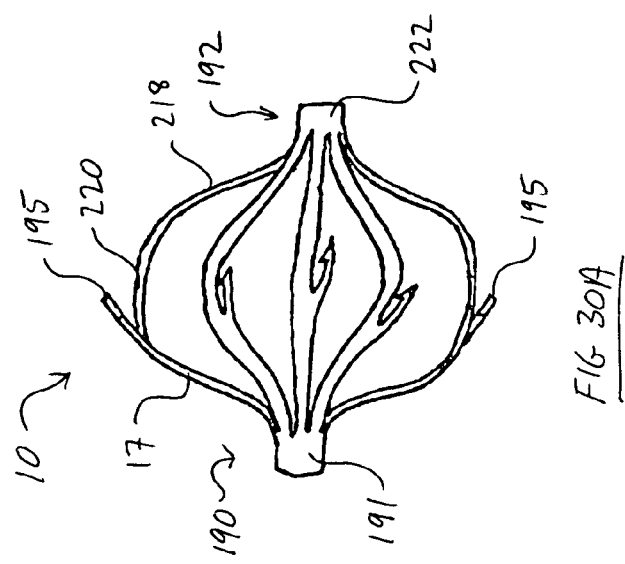
FIGS. 30 and 30A are perspective views of a further occlusion device in accordance with the present invention.
Figure 30:
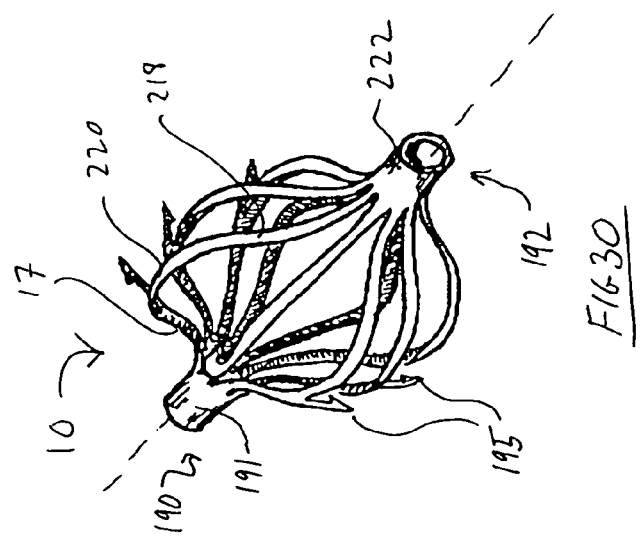
Figure 33:
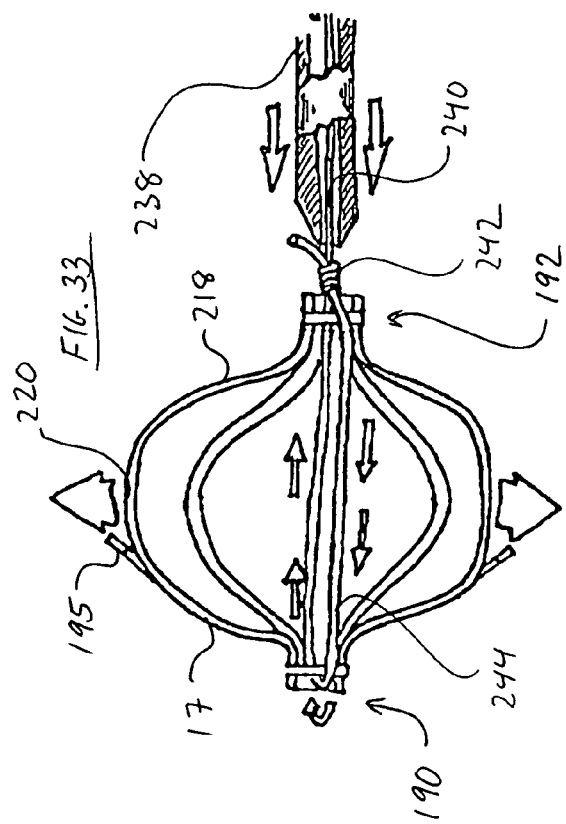
FIG. 33 is a schematic view of a pull string deployment embodiment of the occlusion device of FIG. 30.
Figure 32:
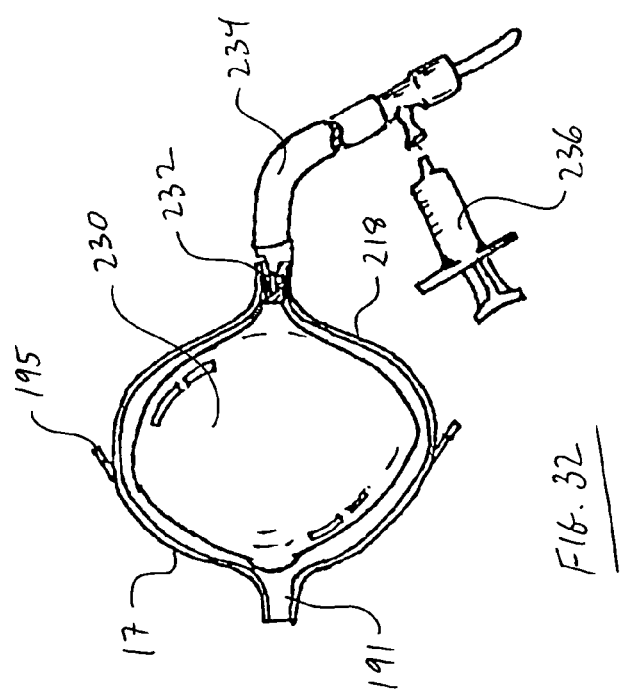
FIG. 32 is a schematic illustration of an inflatable balloon positioned within the occlusion device of FIG. 30.

The occlusion device 10 illustrated in FIG. 30 may be constructed in any of a variety of ways, as will become apparent to those of skill in the art in view of the disclosure herein. In one preferred method, the occlusion device 10 is constructed by laser cutting a piece of tube stock to provide a plurality of axially extending slots in-between adjacent supports 228. Similarly, each barb 195 can be laser cut from the corresponding support 228 or space in-between adjacent supports 228. The generally axially extending slots which separate adjacent supports 228 end a sufficient distance from each of the proximal end 192 and distal end 190 to leave a proximal hub 222 and a distal hub 191 to which each of the supports 228 will attach. In this manner, an integral cage structure may be formed. Alternatively, each of the components of the cage structure may be separately formed and attached together such as through soldering, heat bonding, adhesives, and other fastening techniques which are known in the art. A further method of manufacturing the occlusion device 10 is to laser cut a slot pattern on a flat sheet of appropriate material, such as a flexible metal or polymer, as has been discussed in connection with previous embodiments. The flat sheet may thereafter be rolled about an axis and opposing edges bonded together to form a tubular structure.

The apex portion 220 which carries the barb 195 may be advanced from a low profile orientation in which each of the supports 228 extend generally parallel to the longitudinal axis, to an implanted orientation as illustrated, in which the apex 220 and the barb 195 are positioned radially outwardly from the longitudinal axis. The support 228 may be biased towards the enlarged orientation, or may be advanced to the enlarged orientation following positioning within the tubular anatomical structure, in any of a variety of manners. For example, referring to FIG. 32, an inflatable balloon 230 is positioned within the occlusion device 10. Inflatable balloon 230 is connected by way of a removable coupling 232 to an inflation catheter 234. Inflation catheter 234 is provided with an inflation lumen for providing communication between an inflation media source 236 outside of the patient and the balloon 230. Following positioning within the target body lumen, the balloon 230 is inflated, thereby engaging barbs 195 with the surrounding tissue. The inflation catheter 234 is thereafter removed, by decoupling the removable coupling 232, and the inflation catheter 234 is thereafter removed.

In an alternate embodiment, the supports 228 are radially enlarged such as through the use of a deployment catheter 238. Deployment catheter 238 comprises a lumen for movably receiving a deployment line 240. Deployment line 240 extends in a loop 244 formed by a slip knot 242. As will be apparent from FIG. 33, proximal retraction on the deployment line 240 will cause the distal hub 191 to be drawn towards the proximal hub 222, thereby radially enlarging the cross-sectional area of the occlusion device 10. Depending upon the material utilized for the occlusion device 10, the supports 228 will retain the radially enlarged orientation by elastic deformation, or may be retained in the enlarged orientation such as by securing the slip knot 242 immovably to the deployment line 240 at the fully radially enlarged orientation. This may be accomplished in any of a variety of ways, using additional knots, clips, adhesives, or other techniques known in the art.

Figure 34B:
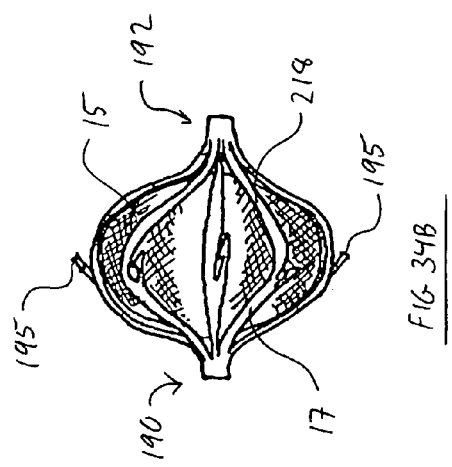
FIGS. 34A and 34B are side elevational schematic representations of partial and complete barrier layers on the occlusion device of FIG. 30.
Figure 34A:
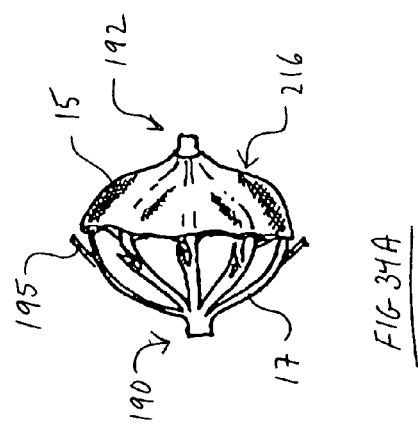

Referring to FIGS. 34A and 34B, the occlusion device 10 may be provided with a barrier 15 such as a mesh or fabric as has been previously discussed. Barrier 15 may be provided on only one hemisphere such as proximal face 216, or may be carried by the entire occlusion device 10 from proximal end 192 to distal end 190. The barrier may be secured to the radially inwardly facing surface of the supports 228, as illustrated in FIG. 34B, or may be provided on the radially outwardly facing surfaces of supports 228, or both.

Figure 35:
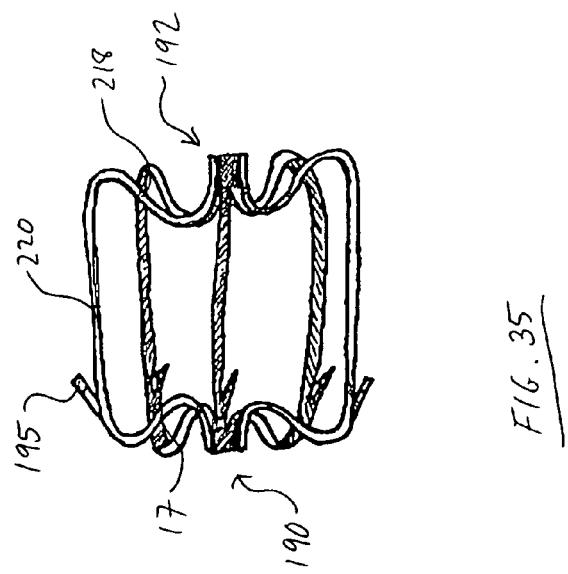
FIG. 35 is a side elevational schematic view of an alternate occlusion device in accordance with the present invention.

A further embodiment of the occlusion device 10 is illustrated in FIG. 35, in which the apex 220 is elongated in an axial direction to provide additional contact area between the occlusion device 10 and the wall of the tubular structure. In this embodiment, one or two or three or more anchors 195 may be provided on each support 228, depending upon the desired clinical performance. The occlusion device 10 illustrated in FIG. 35 may also be provided with any of a variety of other features discussed herein, such as a partial or complete barrier 15 covering. In addition, the occlusion device 10 illustrated in FIG. 35 may be enlarged using any of the techniques disclosed elsewhere herein.

While particular forms of the invention have been described, it will be apparent that various modifications can be made without departing from the spirit and scope of the invention. Accordingly, it is not intended that the invention be limited, except as by the appended claims.

What is claimed is:

1. A containment device for positioning at a left atrial appendage, comprising:
   a proximal end, a distal end, an intermediate portion between the proximal and distal ends, and a longitudinal axis extending therethrough;
   at least three supports extending between the proximal end and the distal end;
   each support comprising an elongate, flexible element which is movable from a first orientation in which the element extends substantially parallel to the axis at no more than a first distance from the axis, to a second orientation in which at least a portion of the element is inclined toward the intermediate portion with respect to the axis and is separated by at least a second distance from the axis which is greater than the first distance, wherein the intermediate portion in the second orientation is sized and configured to engage a surface at the left atrial appendage and the supports in their second orientation increase radially in dimension from the proximal end to an apex portion and then decrease radially in dimension from the apex portion to the distal end; and
   an endothelialization membrane carried by the device, for promoting endothelialization across the left atrial appendage,
   wherein the endothelialization membrane at least in part comprises a first membrane on a first side of the supports, a second membrane on a second side of the supports, and a bonding layer for bonding the first membrane and the second membrane together.

2. A containment device as in claim 1, comprising at least five supports.

3. A containment device as in claim 1, comprising from about five supports to about twenty supports.

4. A containment device as in claim 3, further comprising at least one barb on each of at least two supports.

5. A containment device as in claim 1, further comprising a proximal hub at the proximal end and a distal hub at the distal end.

6. A containment device as in claim 5, wherein the supports and the proximal hub and the distal hub are formed from a tube.

7. A containment device as in claim 5, wherein the supports and the proximal hub and the distal hub are formed from a sheet.

8. A containment device as in claim 1, further comprising at least one barb on each support.

9. A containment device as in claim 1, wherein the supports comprise a nickel titanium alloy.

10. A containment device as in claim 1, wherein the supports comprise stainless steel.

11. A containment device as in claim 1, wherein the first and second membranes comprise ePTFE.

12. A containment device as in claim 1, wherein the first and second membranes comprise Dacron.

13. A containment device as in claim 1, where the first and second membranes comprise nylon.

14. A containment device as in claim 1, wherein the endothelialization membrane has a pore size of no greater than about 0.04 inches.

15. A containment device as in claim 1, wherein the containment device comprises a self expandable structure.

16. A containment device as in claim 15, wherein the self expandable structure comprises wire mesh.

17. A containment device as in claim 15, wherein the self expandable structure comprises braided wire.

18. A containment device as in claim 15, wherein the self expandable structure comprises wire coil.

19. A containment device as in claim 15, wherein the self expandable structure comprises shape memory material.

20. A containment device as in claim 15, wherein the self expandable structure comprises pseudoelastic alloy.

21. A containment device as in claim 15, wherein the self expandable structure comprises nickel titanium alloy.

22. A containment device as in claim 15, wherein the self expandable structure comprises stainless steel.

23. A containment device as in claim 15, wherein the self expandable structure comprises composite material.

24. A containment device as in claim 1, wherein the containment device comprises a self expandable wire structure.

25. A containment device for implantation at an opening in the body, comprising:
    a support member movable from a reduced cross-section to an enlarged cross-section, the support member in the enlarged cross-section extending from a proximal end and inclining radially outward to an apex portion, and then inclining radially inward to a distal end; and
    a porous endothelialization membrane carried by the support member,
    wherein the endothelialization membrane at least in part comprises a first membrane on a first side of the support member, a second membrane on a second side of the support member, and a bonding layer for bonding the first membrane and the second membrane together.

26. A containment device as in claim 25, further comprising at least one hub on the support member and a plurality of spokes extending therefrom.

27. A containment device as in claim 26, wherein the support member comprises at least eight spokes.

28. A containment device as in claim 26, wherein at least one spoke has a first end and a second end, and the first end is attached to the hub.

29. A containment device as in claim 26, wherein each spoke comprises a proximal section, a distal section, and a bend in between the proximal and distal sections when the support member is in the enlarged cross-section.

30. A containment device as in claim 26, wherein the spokes are cut from a tube.

31. A containment device as in claim 26, comprising at least one barb on each spoke.

32. A containment device as in claim 26, wherein the spokes comprise a nickel titanium alloy.

33. A containment device as in claim 26, wherein the spokes comprise stainless steel.

34. A containment device as in claim 25, wherein the support member comprises wire.

35. A containment device as in claim 25, further comprising at least one tissue attachment element on the support.

36. A containment device as in claim 35, wherein the tissue attachment element comprises a tissue piercing element.

37. A containment device as in claim 25, further comprising at least one tissue attachment element on the support member.

38. A containment device as in claim 25, wherein the first and second membranes comprise ePTFE.

39. A containment device as in claim 25, wherein the first and second membranes comprises Dacron.

40. A containment device as in claim 25, where the first and second membranes comprises nylon.

41. A containment device as in claim 25, wherein the endothelialization membrane has a pore size of no greater than about 0.04 inches.

42. A containment device as in claim 25, wherein the containment device comprises a self expandable structure.

43. A containment device as in claim 42, wherein the containment device comprises a self expandable wire structure.

44. A containment device as in claim 42, wherein the self expandable structure comprises wire mesh.

45. A containment device as in claim 42, wherein the self expandable structure comprises braided wire.

46. A containment device as in claim 42, wherein the self expandable structure comprises wire coil.

47. A containment device as in claim 42, wherein the self expandable structure comprises shape memory material.

48. A containment device as in claim 42, wherein the self expandable structure comprises pseudoelastic alloy.

49. A containment device as in claim 42, wherein the self expandable structure comprises nickel titanium alloy.

50. A containment device as in claim 42, wherein the self expandable structure comprises stainless steel.

51. A containment device as in claim 42, wherein the self expandable structure comprises composite material.

52. A containment device as in claim 42, wherein the self expandable structure has at least one proximally concave surface and at least one distally concave surface when in an expanded configuration.

53. A containment device as in claim 25, wherein the bonding layer comprises a mesh.

54. A containment device as in claim 53, wherein the mesh comprises polyethylene.

55. A containment device as in claim 54, wherein the mesh has an open surface area within the range of from about 10% to about 90%.

56. A containment device as in claim 54, wherein the mesh has an open surface area within the range of from about 30% to about 60%.

57. A containment device as in claim 25, wherein the device in its enlarged cross-section has a maximum transverse dimension adapted to engage a surface at a left atrial appendage.

58. A containment device as in claim 25, wherein the apex portion is elongated in an axial direction.

59. A device for implantation within a left atrial appendage of a patient, the device comprising:

an expandable frame having a proximal end, a distal end, and a longitudinal axis extending therethrough, the frame comprising a plurality of supports;

each support comprising an elongate, flexible element, at least some of the supports being movable from a first orientation in which the element extends substantially parallel to the axis at no more than a first distance from the axis, to a second orientation in which at least a portion of the element is inclined with respect to the axis and is separated by at least a second distance from the axis which is greater than the first distance, wherein the supports in their second orientation increase radially in dimension from the proximal end to an apex portion and then decrease radially in dimension from the apex portion to the distal end; and an endothelialization membrane attached to at least a proximal face of the device having a pore size sufficient to permit endothelialization, the proximal face of the device comprising at least in part the inclined portion of a plurality of the flexible elements and being sized and configured to block an opening to the left atrial appendage;

wherein the endothelialization membrane has a porosity in the range of about 5 to about 60 microns;

wherein the endothelialization membrane comprises a first membrane and a second membrane, wherein the first membrane and second membrane are attached to each other on opposite sides of the supports.

60. The device of claim 59, further comprising a proximal hub at the proximal end and a distal hub at the distal end.

61. The device of claim 59, wherein the supports comprise a nickel titanium alloy.

62. The device of claim 59, wherein the membrane comprises ePTFE.

* * * * *

UNITED STATES PATENT AND TRADEMARK OFFICE
CERTIFICATE OF CORRECTION

| | | |
|---|---|---|
| PATENT NO. | : 7,128,073 B1 | Page 1 of 1 |
| APPLICATION NO. | : 09/435562 | |
| DATED | : October 31, 2006 | |
| INVENTOR(S) | : Erik J. Van Der Burg et al. | |

It is certified that error appears in the above-identified patent and that said Letters Patent is hereby corrected as shown below:

Title Page, Item (75) (second inventor's residence) at line 2, After "Cicco," delete "Sunnyvale" and insert -- San Jose --, therefor.

Title Page, Item (75) (fourth inventor's name) at line 5, Delete "Khairkahan" and insert -- Khairkhahan --, therefor.

Title Page, Item (75) (fifth inventor's name) at line 6, Delete "Kriedler" and insert -- Kreidler --, therefor.

In column 12, at line 60, Delete "601" and insert -- 60 --, therefor.

Signed and Sealed this

Twenty-fourth Day of July, 2007

JON W. DUDAS
*Director of the United States Patent and Trademark Office*